US012326451B2

United States Patent
Van Der Werf et al.

(10) Patent No.: US 12,326,451 B2
(45) Date of Patent: *Jun. 10, 2025

(54) SEVERE ACUTE RESPIRATORY SYNDROME (SARS)—ASSOCIATED CORONAVIRUS DIAGNOSTICS

(71) Applicant: INSTITUT PASTEUR, Paris (FR)

(72) Inventors: Sylvie Van Der Werf, Paris (FR); Nicolas Escriou, Paris (FR); Caroline Demeret, Paris (FR); Stéphane Petres, Paris (FR); Pierre Lafaye, Paris (FR); Jacques Bellalou, Paris (FR)

(73) Assignee: INSTITUT PASTEUR, Paris (FR)

( * ) Notice: Subject to any disclaimer, the term of this patent is extended or adjusted under 35 U.S.C. 154(b) by 1265 days.

This patent is subject to a terminal disclaimer.

(21) Appl. No.: 16/936,752

(22) Filed: Jul. 23, 2020

(65) Prior Publication Data

US 2021/0311054 A1 Oct. 7, 2021

Related U.S. Application Data

(60) Provisional application No. 63/003,855, filed on Apr. 1, 2020.

(51) Int. Cl.
| | | |
|---|---|---|
| *G01N 33/569* | (2006.01) | |
| *C07K 14/005* | (2006.01) | |
| *C12N 15/70* | (2006.01) | |

(52) U.S. Cl.
CPC ..... *G01N 33/56983* (2013.01); *C07K 14/005* (2013.01); *C12N 15/70* (2013.01); *C12N 2770/20022* (2013.01); *C12N 2770/20031* (2013.01); *G01N 2333/165* (2013.01); *G01N 2800/26* (2013.01)

(58) Field of Classification Search
CPC .............. G01N 33/569; C12N 15/70
See application file for complete search history.

(56) References Cited

U.S. PATENT DOCUMENTS

| | | | | |
|---|---|---|---|---|
| 8,343,718 | B2 * | 1/2013 | Van Der Werf | A61K 39/12 435/7.1 |
| 11,001,901 | B1 * | 5/2021 | Donati | C12Q 1/6883 |
| 2009/0011000 | A1 * | 1/2009 | Hinz | C07K 14/005 435/243 |
| 2016/0015702 | A1 | 1/2016 | Huber | |

OTHER PUBLICATIONS

Zhang et al., Evaluation of Recombinant Nucleocapsid and Spike Proteins for Serological Diagnosis of Novel Coronavirus Disease 2019 (COVID-19). medRxiv, Preprint : PPR118185, Mar. 2020, 1-28 (Year: 2020).*

To et al., Temporal Profiles of Viral Load in Posterior Oropharyngeal Saliva Samples and Serum Antibody Responses During Infection by SARS-CoV-2: An Observational Cohort Study, 2020, 20, 565-574. (Year: 2020).*

To et al., Temporal profiles of viral load in posterior oropharyngeal saliva samples and serum antibody responses during infection by SARS-CoV-2: an observational cohort study Infectious Disease, Supplementary Index, The Lancet, Appendix, 2020, 1-10. (Year: 2020).*

Sigma-Aldrich, pET-28b(+)—Novagen, Millipore Sigma, 2024, 1-3. Obtained online at: https://www.sigmaaldrich.com/US/en/product/mm/69865m?srsltid=AfmBOorX076TmutlAskbQGiuW_WiP88y5fW6icljotCjVVU0hH6iGA54 on Nov. 22, 2024. (Year: 2024).*

Addgene, WT N-His Ana GvpC in pET28a, Addgene, 2020, 1-4. Obtained online at: https://www.addgene.org/search/catalog/plasmids/?q=pet28a+vector&page_number=1&page_size=40 on Nov. 22, 2024). (Year: 2024).*

NovoPro, pET-28a(+) vector (V011005), NovoPro Bioscience, 2025, 1-7. Obtained online at: https://www.novoprolabs.com/vector/V11005#:~:text=pET-28a(+)%20is%20a,to%20remove%20the%His-tag on Mar. 31, 2025. (Year: 2025).*

Guo et al. (Clinical Infectious Diseases. 2020; 71 (15): 778-785, published online Mar. 21, 2020).

Dummler et al. (Microbial Cell Factories. 2005; 4: 34).

Derwent abstract of Chen et al. (CN 1472318) Feb. 2004.

Lau et al. (Journal of Clinical Microbiology. 2004; 42 (7): 2884-2889).

Grzelak et al. (Science Translational Medicine. Sep. 2, 2020; 12 eabc3103).

* cited by examiner

*Primary Examiner* — Amy M Bunker

(74) *Attorney, Agent, or Firm* — Arrigo, Lee, Guttman & Mouta-Bellum LLP

(57) ABSTRACT

The invention relates to the diagnosis of a SARS-associated coronavirus, such as a SARS-CoV-2 infection and SARS-CoV-1 infection, using the N_SARS-CoV-1 and N_SARS-CoV-2 proteins and antibodies binding to these proteins. The invention reagents, methods and kits for the detection of a SARS-associated coronavirus.

Figure 1A:
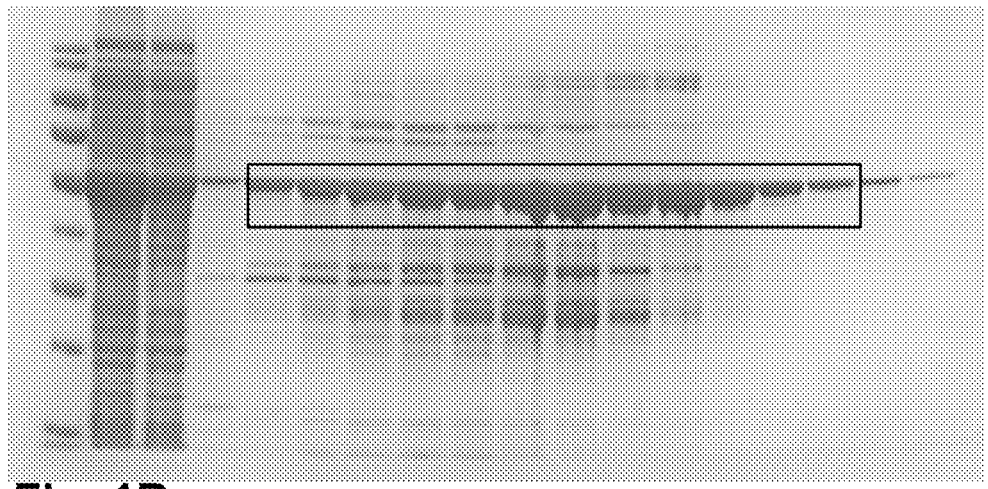

18 Claims, 12 Drawing Sheets
Specification includes a Sequence Listing.

Gels Filtration
n° 5 / 6 / 7 / 8

Gels Filtration
n° 1 / 2 / 3 / 4

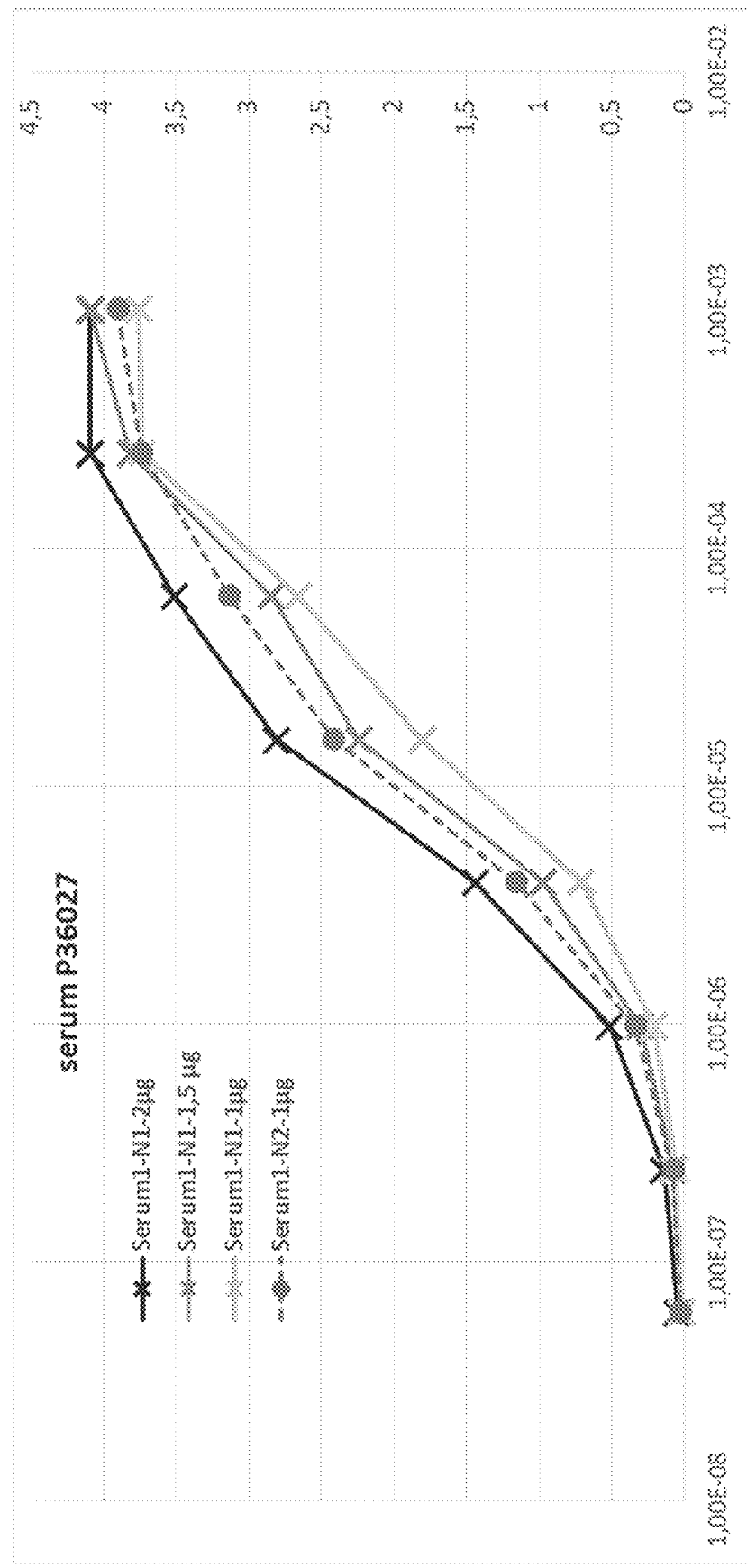

SEQUENCE LISTING

```
<160> NUMBER OF SEQ ID NOS: 1

<210> SEQ ID NO 1
<211> LENGTH: 445
<212> TYPE: PRT
<213> ORGANISM: Severe acute respiratory syndrome (SARS)-associated
      coronavirus-2

<400> SEQUENCE: 1

Met Lys His His His His His His Pro Met Ser Asp Tyr Asp Ile Pro
1               5                   10                  15

Thr Thr Glu Asn Leu Tyr Phe Gln Gly Ala Met Ser Asp Asn Gly Pro
            20                  25                  30

Gln Asn Gln Arg Asn Ala Pro Arg Ile Thr Phe Gly Gly Pro Ser Asp
        35                  40                  45

Ser Thr Gly Ser Asn Gln Asn Gly Glu Arg Ser Gly Ala Arg Ser Lys
    50                  55                  60

Gln Arg Arg Pro Gln Gly Leu Pro Asn Asn Thr Ala Ser Trp Phe Thr
65                  70                  75                  80

Ala Leu Thr Gln His Gly Lys Glu Asp Leu Lys Phe Pro Arg Gly Gln
                85                  90                  95

Gly Val Pro Ile Asn Thr Asn Ser Ser Pro Asp Asp Gln Ile Gly Tyr
            100                 105                 110

Tyr Arg Arg Ala Thr Arg Arg Ile Arg Gly Gly Asp Gly Lys Met Lys
        115                 120                 125

Asp Leu Ser Pro Arg Trp Tyr Phe Tyr Tyr Leu Gly Thr Gly Pro Glu
    130                 135                 140

Ala Gly Leu Pro Tyr Gly Ala Asn Lys Asp Gly Ile Ile Trp Val Ala
145                 150                 155                 160

Thr Glu Gly Ala Leu Asn Thr Pro Lys Asp His Ile Gly Thr Arg Asn
                165                 170                 175

Pro Ala Asn Asn Ala Ala Ile Val Leu Gln Leu Pro Gln Gly Thr Thr
            180                 185                 190

Leu Pro Lys Gly Phe Tyr Ala Glu Gly Ser Arg Gly Gly Ser Gln Ala
        195                 200                 205

Ser Ser Arg Ser Ser Ser Arg Ser Arg Asn Ser Ser Arg Asn Ser Thr
    210                 215                 220

Pro Gly Ser Ser Arg Gly Thr Ser Pro Ala Arg Met Ala Gly Asn Gly
225                 230                 235                 240

Gly Asp Ala Ala Leu Ala Leu Leu Leu Leu Asp Arg Leu Asn Gln Leu
                245                 250                 255

Glu Ser Lys Met Ser Gly Lys Gly Gln Gln Gln Gln Gly Gln Thr Val
            260                 265                 270
```

-continued

```
Thr Lys Lys Ser Ala Ala Glu Ala Ser Lys Lys Pro Arg Gln Lys Arg
        275                 280                 285

Thr Ala Thr Lys Ala Tyr Asn Val Thr Gln Ala Phe Gly Arg Arg Gly
        290                 295                 300

Pro Glu Gln Thr Gln Gly Asn Phe Gly Asp Gln Glu Leu Ile Arg Gln
305                 310                 315                 320

Gly Thr Asp Tyr Lys His Trp Pro Gln Ile Ala Gln Phe Ala Pro Ser
                325                 330                 335

Ala Ser Ala Phe Phe Gly Met Ser Arg Ile Gly Met Glu Val Thr Pro
                340                 345                 350

Ser Gly Thr Trp Leu Thr Tyr Thr Gly Ala Ile Lys Leu Asp Asp Lys
        355                 360                 365

Asp Pro Asn Phe Lys Asp Gln Val Ile Leu Leu Asn Lys His Ile Asp
        370                 375                 380

Ala Tyr Lys Thr Phe Pro Pro Thr Glu Pro Lys Lys Asp Lys Lys Lys
385                 390                 395                 400

Lys Ala Asp Glu Thr Gln Ala Leu Pro Gln Arg Gln Lys Lys Gln Gln
                405                 410                 415

Thr Val Thr Leu Leu Pro Ala Ala Asp Leu Asp Asp Phe Ser Lys Gln
                420                 425                 430

Leu Gln Gln Ser Met Ser Ser Ala Asp Ser Thr Gln Ala
        435                 440                 445
```

SEVERE ACUTE RESPIRATORY SYNDROME (SARS)—ASSOCIATED CORONAVIRUS DIAGNOSTICS

CROSS-REFERENCE TO RELATED APPLICATIONS

This application claims the benefit of U.S. Provisional Application 62/566,907, filed Apr. 1, 2020.

SEQUENCE LISTING

The instant application contains a Sequence Listing which has been submitted in ASCII format via EFS-Web and is hereby incorporated by reference in its entirety. Said ASCII copy, created on Aug. 13, 2020, is named DI2020_20_ST25_2.txt and is 4, 193 bytes in size.

FIELD OF THE INVENTION

The invention relates to the diagnosis of syndrome (SARS)-associated coronavirus infections.

BACKGROUND OF THE INVENTION

The present invention relates to a reliable, specific and sensitive serological diagnosis test of a novel strain of severe acute respiratory syndrome (SARS)-associated coronavirus (SARS-CoV-2).

Coronavirus is a virus containing single-stranded RNA, of positive polarity, of approximately 30 kilobases which replicates in the cytoplasm of the host cells; the 5' end of the genome has a capped structure and the 3' end contains a polyA tail. This virus is enveloped and comprises, at its surface, structures called spicules.

The genome comprises the following open reading frames or ORFs, from its 5' end to its 3' end: ORF1a and ORF1b corresponding to the proteins of the transcription-replication complex, and ORF-S, ORF-E, ORF-M and ORF-N corresponding to the structural proteins S, E, M and N. It also comprises ORFs corresponding to proteins of unknown function encoded by: the region situated between ORF-S and ORF-E and overlapping the latter, the region situated between ORF-M and ORF-N, and the region included in ORF-N.

The S protein is a membrane glycoprotein (200-220 kDa) which exists in the form of spicules or spikes emerging from the surface of the viral envelope. It is responsible for the attachment of the virus to the receptors of the host cell and for inducing the fusion of the viral envelope with the cell membrane.

The small envelope protein (E), also called sM (small membrane), which is a nonglycosylated transmembrane protein of about 10 kDa, is the protein present in the smallest quantity in the virion. It plays a powerful role in the coronavirus budding process which occurs at the level of the intermediate compartment in the endoplasmic reticulum and the Golgi apparatus.

The M protein or matrix protein (25-30 kDa) is a more abundant membrane glycoprotein which is integrated into the viral particle by an M/E interaction, whereas the incorporation of S into the particles is directed by an S/M interaction. It appears to be important for the viral maturation of coronaviruses and for the determination of the site where the viral particles are assembled.

The N protein or nucleocapsid protein (45-50 kDa) which is the most conserved among the coronavirus structural proteins is necessary for encapsidating the genomic RNA and then for directing its incorporation into the virion. This protein is probably also involved in the replication of the RNA.

When the host cell is infected, the reading frame (ORF) situated in 5' of the viral genome is translated into a polyprotein which is cleaved by the viral proteases and then releases several nonstructural proteins such as the RNA-dependent RNA polymerase (Rep) and the ATPase helicase (Hel). These two proteins are involved in the replication of the viral genome and in the generation of transcripts which are used in the synthesis of the viral proteins. The mechanisms by which these subgenomic mRNAs are produced are not completely understood; however, recent facts indicate that the sequences for regulation of transcription at the 5' end of each gene represent signals which regulate the discontinuous transcription of the subgenomic mRNAs.

The proteins of the viral membrane (S, E and M proteins) are inserted into the intermediate compartment, whereas the replicated RNA (+strand) is assembled with the N (nucleocapsid) protein. This protein-RNA complex then combines with the M protein contained in the membranes of the endoplasmic reticulum and the viral particles form when the nucleocapsid complex buds into the endoplasmic reticulum. The virus then migrates across the Golgi complex and eventually leaves the cell, for example by exocytosis. The site of attachment of the virus to the host cell is at the level of the S protein.

Coronaviruses are responsible for 15 to 30% of colds in humans and for respiratory and digestive infections in animals, especially cats (FIPV: Feline infectious peritonitis virus), poultry (IBV: Avian infectious bronchitis virus), mice (MHV: Mouse hepatitis virus), pigs (TGEV: Transmissible gastroenterititis virus, PEDV: Porcine Epidemic diarrhea virus, PRCoV: Porcine Respiratory Coronavirus, HEV: Hemagglutinating encephalomyelitis Virus) and bovines (BCoV: Bovine coronavirus).

In 2019, a new coronavirus named SARS-CoV-2 was isolated, in association with cases of severe acute respiratory syndrome (CoVID-19). Liu et al., Viruses. 2020 Jan. 22; 12 (2), which is hereby incorporated by reference. The complete genome sequence of SARS-CoV-2 is available at GenBank accession no. MN975262, which is hereby incorporated by reference.

The sequence of SARS-CoV-2 has been compared to other coronaviruses. Chan et al., Emerg Microbes Infect. 2020; 9 (1): 221-236. Overall, the genome of SARS-CoV-2 has 89% nucleotide identity with bat SARS-like-CoVZXC21 and 82% with that of human SARS-CoV. Id. The organization of the genome is comparable with human SARS-CoV. Id.

New reagents for the detection and diagnosis of SARS-CoV-2 and SARS-CoV, which are sufficiently sensitive and specific, and immunogenic compositions capable of protecting populations against epidemics of SARS-CoV-2 and SARS-CoV (i.e., "SARS-Cov-1") are needed. The present invention fulfills this need.

BRIEF SUMMARY OF THE INVENTION

The invention encompasses reagents, methods and kits for the diagnosis of a SARS-associated coronavirus, such as a SARS-CoV-2 infection and SARS-CoV-1 infection, using the N_SARS-CoV-1 and N_SARS-CoV-2 proteins and antibodies binding to these proteins. The invention encompasses methods and kits for the detection of a SARS-associated coronavirus.

The invention encompasses a method for the detection of a SARS-associated coronavirus in a biological sample comprising providing a N_SARS-CoV-2 protein; providing a biological sample from a patient infected with a SARS-CoV-1 coronavirus; contacting said N_SARS-CoV-2 protein with said biological sample; and visualizing the antigen-antibody complexes formed. Preferably, the method comprises an ELISA. Preferably, the N_SARS-CoV-2 protein comprises or consists of the sequence of SEQ ID NO:1.

The invention encompasses a method for the detection of a SARS-associated coronavirus in a biological sample comprising providing a N_SARS-CoV-1 protein; providing a biological sample from a patient infected with a SARS-CoVCoV-2 coronavirus; contacting said N_SARS-CoV-1 protein with said biological sample; and visualizing the antigen-antibody complexes formed. Preferably, the method comprises an ELISA.

The invention encompasses a kit for the detection of a SARS-Cov-1coronavirus in a biological sample comprising a N_SARS-CoV-2 protein. Preferably, the kit comprises serum from an animal immunized with a N_SARS-CoV-2 protein.

The invention encompasses a kit for the detection of a SARS-CoV-2 coronavirus in a biological sample comprising a N_SARS-CoV-1 protein. Preferably, the kit comprises serum from an animal immunized with a N_SARS-CoV-2 protein.

BRIEF DESCRIPTION OF THE DRAWINGS

FIG. 1A-E illustrates the purification of the recombinant N protein of SARS-CoV-2. A. SDS PAGE analysis of fractions collected from 1st PURIFICATION STEP: AFFINITY MAC (AKTAPure) according to example 1. Peak of the fractions from A5 to C12 are boxed (Estimated quantity on unicorn 162 mg). B to E. 2ND PURIFICATION STEP: Hiload 16/60 Superdex 200 pg column filtration gel according to example 1. Selection of peaks on histograms and integration of peaks for estimation of protein quantity (B and C). SDS-Page Fraction Removal and Deposition on SDS-Page Gel. GEL FILTRATION 3 on AKTA 1 (D). GEL FILTRATION 6 on AKTA 2 (E).

FIG. 2A-B shows the binding on SARS-CoV-2 nucleoprotein (N) of serum and plasma (A) and purified anti-SARS-CoV-2 N polyclonal antibodies (B) from SARS-CoV-2 nucleoprotein (N) immunized alpaca.

FIG. 3A-C shows the comparison of SARS-CoV-2 N and SARS-CoV-1 N indirect ELISA for detection of SARS-CoV-2 infection in patients sera CoVID-01 and CoVID-02:2 CoVID patients hospitalized patients with confirmed SARS-CoV-2 infection (severe cases). Sympt-01 to Sympt-20:20 symptomatic patients with mild CoVID-like symptoms, sampled during symptoms or after symptoms disappearance (NOT tested for viral RNA). Neg Ad-01 and Neg Ad-02:2 prepandemic adults. The assay was performed with various serum dilutions: 1/200 and 1/800 (A); 1/3200 (B); 1/12800 (C).

FIG. 4A-C shows the comparison of SARS-CoV-2 N and SARS-CoV-1 N indirect ELISA for detection of anti SARS-CoV-1 antibodies. A. Various dilutions of a first rabbit hyperimmune serum against SARS-CoV-1 virions (serum 1 or P36027) were tested with 1 μg of SARS-CoV-2 N (N2) or 1 μg, 1.5 μg or 2 μg of SARS-CoV-1 N (N1). B. various dilutions of a second rabbit hyperimmune serum against SARS-CoV-1 virions (serum 2 or P38136) were tested with 1 μg of SARS-CoV-2 N (N2) or 1 pg, 1.5 μg or 2 pg of SARS-CoV-1 (N1). C. Various dilutions of first serum (S+1) and second (S+2) anti-SARS-CoV-1 were tested with 1 pg of SARS-CoV-2 N (N2) or 1 pg, 1.5 μg or 2 μg of SARS-CoV-1 N. (N1). Rabbit pre-immune (pi) and anti-HPV E1 (S) sera were used as negative controls.

FIG. 5 shows a whisker-plot of ELISA on IgG specific of N protein of SARS-CoV-2. IgGs specific of protein N of SARS-CoV-2 have been titrated in serums of the CORSER cohort (n=164; IcareB), in serums of the observation and monitoring protocol of the Intensive Medicine and Resuscitation service of Assistance Publique des Hôpitaux de Paris (APHP) Cochin (n=20) in longitudinal follow-up and in serums and plasma of healthy donors of Etablissement Français du Sang (EFS) sampled in December 2019 (frozen plasmas n=20, frozen serums n=20).

FIG. 6 shows a whisker-plot of ELISA on IgG specific of S protein of SARS-CoV-2.

FIG. 7 shows the correlation between the titration of IgG specific of protein N of SARS-CoV-2 versus IgG specific of protein S of SARS-CoV-2 in serum from APHP-Cochin (n=20) and EFS (n=4).

FIG. 8 shows the correlation between the titration of IgG specific of protein N of SARS-CoV-1 versus IgG specific of protein N of SARS-CoV-2 in serum from APHP-Cochin (n=20) and EFS (n=4).

FIG. 9 shows the correlation between the titration of IgG specific of protein N of SARS-CoV-2 in the quick test (5 min) versus the routine test (120 min)-mean of the values in duplicate.

DETAILED DESCRIPTION OF THE INVENTION

The invention encompasses compositions, kits, uses, and methods for the detection and diagnosis of CoVID-19 and SARS.

The indirect ELISA test was used with serum from SARS-CoV-2 patients with confirmed infections, as well as from various symptomatic patients (untested for SARS-CoV-2 RNA) and presumptively negative patients.

The test was able to detect anti-SARS-CoV-2 antibodies in the serum of all of SARS-CoV-2 patients with confirmed infections, as well as in the serum of many of the symptomatic (untested for SARS-CoV-2 RNA). Anti-SARS-CoV-2 antibodies were not detected in the serum of presumptively negative patients. These experiments showed that the N protein of SARS-CoV-1 ("N_SARS-CoV-1") was able to bind to antibodies present in the serum of SARS-CoV-2 infected individuals. Thus, the antibodies generated against the N protein of SARS-CoV-2 ("N_SARS-CoV-2") by the patients could bind to the N_SARS-CoV-1 protein. This allows the use of the N_SARS-CoV-1, for example using an indirect ELISA, for the detection of SARS-CoV-2 via immunoassay.

The N_SARS-CoV-2 protein of SARS-CoV-2 was produced recombinantly in *E. coli* strain BL21 (DE3) pDIA17. To achieve expression, DNA encoding the N_SARS-CoV-2CoV-2 was codon optimized for expression in bacteria and modified to express a Hiss N-terminal label. The DNA was transformed into *E. coli* and the protein produced was purified using a nickel column.

An indirect ELISA was used to compare plates coated with N_SARS-CoV-2CoV-2 to plates coated with N_SARS-CoV-1 using serum from SARS-CoV-2 patients with confirmed infections, as well as from various symptomatic patients (untested for SARS-CoV-2 RNA) and presumptively negative patients. Both N_SARS-CoV-2 and N_SARS-CoV-1 were able to detect anti-SARS-CoV-2 antibodies in the serum of all of COVID-19 patients with confirmed infections, as well as in the serum of many of the symptomatic (untested for SARS-CoV-2 RNA). Anti-SARS-CoV-2 antibodies were not detected in the serum of presumptively negative patients. The difference between the two proteins was an increased sensitivity with the N_SARS-CoV-2 protein (about 25%). These results were surprising.

Rabbit hyper immune serum against N_SARS-CoV-1 and N_SARS-CoV-2 proteins was generated. Rabbit hyper immune serum against N_SARS-CoV-1 and N_SARS-CoV-2 proteins could bind to both the N_SARS-CoV-1 and N_SARS-CoV-2 proteins.

Alpaca were immunized with N_SARS-CoV-2. Binding of plasma and serum VHH from the immunized alpaca to N_SARS-CoV-2 protein was also detected.

These results allow for the use of the N_SARS-CoV-1 and N_SARS-CoV-2 proteins and antibodies generated against these proteins for the detection of SARS-CoV and SARS-Cov-2 via immunoassay. The high correlation of immunoassay tests with N_SARS-CoV-1 and N_SARS-CoV-2 proteins with low cross-reactivity and high sensitivity indicates that these proteins can be used for immunodiagnostics of patients with of SARS-CoV-1 and SARS-CoV-2. The invention provides expression vectors, proteins, antibodies, and methods and kits containing these reagents.

Expression Vectors

The invention encompasses recombinant vectors. The recombinant vector can be a vector for eukaryotic or prokaryotic expression, such as a plasmid, a phage for bacterium introduction, a YAC able to transform yeast, a viral vector and especially a retroviral vector, or any expression vector. An expression vector as defined herein is chosen to enable the production of an N protein or polyepitope, either in vitro or in vivo.

Preferably, the expression vector expressing the N_SARS-CoV-1 protein is one of the expression vectors described in U.S. Pat. No. 8,343,718, which is hereby incorporated by reference.

In one embodiment, the expression vector comprises an N cDNA cloned into the Expression Vector pIVEX2.3 or pIVEX2.4, as described in U.S. Pat. No. 8,343,718.

In one embodiment, the expression vector is pIV2.3N, particularly as contained in the bacteria transformed with pIV2.3N that were deposited under the terms of the Budapest Treaty at the Collection Nationale de Culture de Microorganismes (CNCM) on Oct. 23, 2003, under the number 1-3117.

In one embodiment, the expression vector is pETM11/N-nCov E. coli 3-(His)6-Nter.

In one embodiment, the expression vector encodes a protease cleavage site, such as TEV cleave site, inserted between N protein coding sequence and a protein purification Tag, such as polyHis tag. In a preferred embodiment, the expression vector encodes a His tag. In one embodiment, a TEV cleavage site is positioned to remove the His tag, for example, after purification.

The expression vector can comprise transcription regulation regions (including promoter, enhancer, ribosome binding site (RBS), polyA signal), a termination signal, a prokaryotic or eukaryotic origin of replication and/or a selection gene. The features of the promoter can be easily determined by the man skilled in the art in view of the expression needed, i.e., constitutive, transitory or inducible (e.g. IPTG), strong or weak, tissue-specific and/or developmental stage-specific promoter. The vector can also comprise sequence enabling conditional expression, such as sequences of the Cre/Lox system or analogue systems.

In various embodiments, the expression vector is a plasmid, a phage for bacterium introduction, a YAC able to transform yeast, a viral vector, or any expression vector. An expression vector as defined herein is chosen to enable the production of a protein or polyepitope, either in vitro or in vivo.

The nucleic acid molecules according to the invention can be obtained by conventional methods, known per se, following standard protocols such as those described in Current Protocols in Molecular Biology (Frederick M. AUSUBEL, 2000, Wiley and son Inc., Library of Congress, USA). For example, they may be obtained by amplification of a nucleic sequence by PCR or RT-PCR or alternatively by total or partial chemical synthesis.

The vectors are constructed and introduced into host cells by conventional recombinant DNA and genetic engineering methods which are known per se. Numerous vectors into which a nucleic acid molecule of interest may be inserted in order to introduce it and to maintain it in a host cell are known per se; the choice of an appropriate vector depends on the use envisaged for this vector (for example replication of the sequence of interest, expression of this sequence, maintenance of the sequence in extrachromosomal form or alternatively integration into the chromosomal material of the host), and on the nature of the host cell.

N_SARS-CoV-1 & N_SARS-CoV-2 Proteins

Preferably, the N_SARS-CoV-2 protein comprises the amino acid sequence of the SARS-CoV-2 N protein of NCBI QHO62884.1.

Preferably, the N_SARS-CoV-1 protein comprises the amino acid sequence of the SARS-CoV N protein of NP_828858, which is hereby incorporated by reference.

Preferably, the N_SARS-CoV-2 protein comprises the following amino acid sequence.

(SEQ ID NO: 1)

```
  1  MKHHHHHHPM SDYDIPTTEN LYFQGAMSDN GPQNQRNAPR ITFGGPSDST GSNQNGERSG

61  ARSKQRRPQG LPNNTASWFT ALTQHGKEDL KFPRGQGVPI NTNSSPDDQI GYYRRATRRI

121  RGGDGKMKDL SPRWYFYYLG TGPEAGLPYG ANKDGIIWVA TEGALNTPKD HIGTRNPANN

181  AAIVLQLPQG TTLPKGFYAE GSRGGSQASS RSSSRSRNSS RNSTPGSSRG TSPARMAGNG

241  GDAALALLLL DRLNQLESKM SGKGQQQQGQ TVTKKSAAEA SKKPRQKRTA TKAYNVTQAF

301  GRRGPEQTQG NFGDQELIRQ GTDYKHWPQI AQFAPSASAF GMSRIGMEV TPSGTWLTYT

361  GAIKLDDKDP NFKDQVILLN KHIDAYKTFP PTEPKKDKKK KADETQALPQ RQKKQQTVTL

421  LPAADLDDFS KQLQQSMSSA DSTQA**.
```

Preferably, the N_SARS-CoV-1 protein is one of the N proteins described in U.S. Pat. No. 8,343,718, particularly SEQ ID NO:37, which is hereby incorporated by reference.

In one embodiment, the N_SARS-CoV-1 protein is produced by bacteria transformed with pIV2.3N, which were deposited under the terms of the Budapest Treaty at the Collection Nationale de Culture de Microorganismes (CNCM) on Oct. 23, 2003, under the number 1-3117. The address of CNCM is: Collection Nationale de Culture de Microorganismes, Institut Pasteur, 28 rue du Dr Roux, 75724 Paris CEDEX 15, France.

In one embodiment, the N_SARS-CoV-2 protein is produced by bacteria transformed with the expression vector pETM11/N-nCov E. coli 3-(His)$_{6-Nter}$.

In one embodiment the expression vector is contained within one of the following bacterial strains:

E. coli B BL21 (DE3) pDIA17 pLA131 I-2722
E. coli B BL21 (DE3) pDIA17 pLA134 I-2723
E. coli B BL21 (DE3) pDIA17 pLA631 I-2724
E. coli B BL21 (DE3) pDIA17 pLA634 I-2725
E. coli B BL21 (DE3) pDIA17 pLA131 I-2830.

These strains were deposited under the terms of the Budapest Treaty at the Collection Nationale de Culture de Microorganismes (CNCM) on Oct. 23, 2003, under the numbers I-2722, I-2723, I-2724, and I-2725 on Sep. 10, 2001 and I-2830 on Feb. 4, 2002.

The invention encompasses "isolated or purified" N_SARS-CoV-1 & N_SARS-CoV-2 proteins. The terms "isolated or purified" mean modified "by the hand of humans" from the natural state; in other words if an object exists in nature, it is said to be isolated or purified if it is modified or extracted from its natural environment or both. For example, a polynucleotide or a protein/peptide naturally present in a living organism is neither isolated nor purified; on the other hand, the same polynucleotide or protein/peptide separated from coexisting molecules in its natural environment, obtained by cloning, amplification and/or chemical synthesis is isolated for the purposes of the present invention. Furthermore, a polynucleotide or a protein/peptide which is introduced into an organism by transformation, genetic manipulation or by any other method, is "isolated" even if it is present in said organism. The term purified as used in the present invention means that the proteins/peptides according to the invention are essentially free of association with the other proteins or polypeptides, as is for example the product purified from the culture of recombinant host cells or the product purified from a nonrecombinant source.

Methods for Making N_SARS-CoV-1 & N_SARS-CoV-2

Production of the N_SARS-CoV-1 & N_SARS-CoV-2 proteins can be achieved by any technique known to the skilled artisan, for example, as detailed in the examples or as described in in U.S. Pat. No. 8,343,718.

The invention also encompasses an N_SARS-CoV-2 protein made by the processes disclosed herein, particularly in Example 1.

Antibodies Against N1 or N2

In one embodiment, polyclonal or monoclonal antibodies are generated in rabbits or mice.

In one embodiment VHH antibodies are generated, for example in alpaca.

The invention encompasses a polyclonal or monoclonal antibody or fragment thereof directed against N_SARS-CoV-1 & N_SARS-CoV-2 protein.

In one embodiment, antibodies can be obtained by immunization of an animal with a N_SARS-CoV-1 & N_SARS-CoV-2 protein.

The antibodies can serve as reagents to bind to native N_SARS-CoV-1 & N_SARS-CoV-2 proteins of patients in immunoassays.

The antibodies can serve as positive control reagents to bind to isolated and purified N_SARS-CoV-1 & N_SARS-CoV-2 proteins in immunoassays of patients.

The antibodies can be used to determine and adjust the concentration of N2 bound to the ELISA plates for serum dilution.

The invention encompasses the polyclonal antibodies, monoclonal antibodies, chimeric antibodies, and fragments thereof (e.g., Fab, Fv, scFv) directed against the N protein.

For the purposes of the present invention, the expression chimeric antibody is understood to mean, in relation to an antibody of a particular animal species or of a particular class of antibody, an antibody comprising all or part of a heavy chain and/or of a light chain of an antibody of another animal species or of another class of antibody.

In some embodiments, purified proteins are used to produce antibodies by conventional techniques. In some embodiments, recombinant or synthetic proteins or peptides are used to produce antibodies by conventional techniques.

Antibodies can be synthetic, semi-synthetic, monoclonal, or polyclonal and can be made by techniques well known in the art. Such antibodies specifically bind to proteins and polypeptides via the antigen-binding sites of the antibody (as opposed to non-specific binding). Purified or synthetic proteins and peptides can be employed as immunogens in producing antibodies immunoreactive therewith. The proteins and peptides contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, Immuno Biology 3:9 (Garland Publishing Inc., 2nd ed. 1996). Because folded proteins have complex surfaces, the number of epitopes available is quite numerous; however, due to the conformation of the protein and steric hinderances, the number of antibodies that actually bind to the epitopes is less than the number of available epitopes (C. A. Janeway, Jr. and P. Travers, Immuno Biology 2:14 (Garland Publishing Inc., 2nd ed. 1996)). Epitopes can be identified by any of the methods known in the art. Such epitopes or variants thereof can be produced using techniques well known in the art such as solid-phase synthesis, chemical or enzymatic cleavage of a polypeptide, or using recombinant DNA technology.

Antibodies are defined to be specifically binding if they bind proteins or polypeptides with a Ka of greater than or equal to about $10^7$ M$^{-1}$. Affinities of binding partners or antibodies can be readily determined using conventional techniques, for example those described by Scatchard et al., Ann. N.Y. Acad. Sci., 51:660 (1949).

Polyclonal antibodies can be readily generated from a variety of sources, for example, horses, cows, goats, sheep, dogs, chickens, alpaca, camels, rabbits, mice, or rats, using procedures that are well known in the art. In general, a purified protein or polypeptide that is appropriately conjugated is administered to the host animal typically through parenteral injection. The immunogenicity can be enhanced through the use of an adjuvant, for example, Freund's complete or incomplete adjuvant. Following booster immunizations, small samples of serum are collected and tested for reactivity to proteins or polypeptides. Examples of various assays useful for such determination include those described in Antibodies: A Laboratory Manual, Harlow and Lane (eds.), Cold Spring Harbor Laboratory Press, 1988; as well as procedures, such as countercurrent immuno-electro-phoresis (CIEP), radioimmunoassay, radio-immunoprecipitation, enzyme-linked immunosorbent assays (ELISA), dot blot assays, and sandwich assays. See U.S. Pat. Nos. 4,376,110 and 4,486,530.

Monoclonal antibodies can be readily prepared using well known procedures. See, for example, the procedures described in U.S. Pat. Nos. RE 32,011, 4,902,614, 4,543,439, and 4,411,993; Monoclonal Antibodies, Hybridomas: A New Dimension in Biological Analyses, Plenum Press, Kennett, Mckeam, and Bechtol (eds.), 1980.

For example, the host animals, such as mice, can be injected intraperitoneally at least once and preferably at least twice at about 3 week intervals with isolated and purified proteins or conjugated polypeptides, for example a peptide comprising or consisting of the specific amino acids set forth above. Mouse sera are then assayed by conventional dot blot technique or antibody capture (ABC) to determine which animal is best to fuse. Approximately two to three weeks later, the mice are given an intravenous boost of the protein or polypeptide. Mice are later sacrificed, and spleen cells fused with commercially available myeloma cells, such as Ag8.653 (ATCC), following established protocols. Briefly, the myeloma cells are washed several times in media and fused to mouse spleen cells at a ratio of about three spleen cells to one myeloma cell. The fusing agent can be any suitable agent used in the art, for example, polyethylene glycol (PEG). Fusion is plated out into plates containing media that allows for the selective growth of the fused cells. The fused cells can then be allowed to grow for approximately eight days. Supernatants from resultant hybridomas are collected and added to a plate that is first coated with goat anti-mouse Ig. Following washes, a label, such as a labeled protein or polypeptide, is added to each well followed by incubation. Positive wells can be subsequently detected. Positive clones can be grown in bulk culture and supernatants are subsequently purified over a Protein A column (Pharmacia).

The monoclonal antibodies of the invention can be produced using alternative techniques, such as those described by Alting-Mees et al., "Monoclonal Antibody Expression Libraries: A Rapid Alternative to Hybridomas", Strategies in Molecular Biology 3:1-9 (1990), which is incorporated herein by reference. Similarly, binding partners can be constructed using recombinant DNA techniques to incorporate the variable regions of a gene that encodes a specific binding antibody. Such a technique is described in Larrick et al., Biotechnology, 7:394 (1989).

Antigen-binding fragments of such antibodies, which can be produced by conventional techniques, are also encompassed by the present invention. Examples of such fragments include, but are not limited to, Fab and F(ab')2 fragments. Antibody fragments and derivatives produced by genetic engineering techniques are also provided.

The monoclonal antibodies of the present invention include chimeric antibodies, e.g., humanized versions of murine monoclonal antibodies. Such humanized antibodies can be prepared by known techniques, and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment can comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (Nature 332:323, 1988), Liu et al. (PNAS 84:3439, 1987), Larrick et al. (Bio/Technology 7:934, 1989), and Winter and Harris (TIPS 14:139, May 1993). Procedures to generate antibodies transgenically can be found in GB 2,272,440, U.S. Pat. Nos. 5,569,825 and 5,545,806.

Antibodies produced by genetic engineering methods, such as chimeric and humanized monoclonal antibodies, comprising both human and non-human portions, which can be made using standard recombinant DNA techniques, can be used. Such chimeric and humanized monoclonal antibodies can be produced by genetic engineering using standard DNA techniques known in the art, for example using methods described in Robinson et al. International Publication No. WO 87/02671; Akira, et al. European Patent Application 0184187; Taniguchi, M., European Patent Application 0171496; Morrison et al. European Patent Application 0173494; Neuberger et al. PCT International Publication No. WO 86/01533; Cabilly et al. U.S. Pat. No. 4,816,567; Cabilly et al. European Patent Application 0125023; Better et al., Science 240:1041 1043, 1988; Liu et al., PNAS 84:3439 3443, 1987; Liu et al., J. Immunol. 139:3521 3526, 1987; Sun et al. PNAS 84:214 218, 1987; Nishimura et al., Canc. Res. 47:999 1005, 1987; Wood et al., Nature 314:446 449, 1985; and Shaw et al., J. Natl. Cancer Inst. 80:1553 1559, 1988); Morrison, S. L., Science 229: 1202 1207, 1985; Oi et al., BioTechniques 4:214, 1986; Winter U.S. Pat. No. 5,225,539; Jones et al., Nature 321:552 525, 1986; Verhoeyan et al., Science 239:1534, 1988; and Beidler et al., J. Immunol. 141:4053 4060, 1988.

In connection with synthetic and semi-synthetic antibodies, such terms are intended to cover but are not limited to antibody fragments, isotype switched antibodies, humanized antibodies (e.g., mouse-human, human-mouse), hybrids, antibodies having plural specificities, and fully synthetic antibody-like molecules.

In one embodiment, the invention encompasses single-domain antibodies (sdAb), also known as NANOBODIES. A sdAb is a fragment consisting of a single monomeric variable antibody domain that can bind selectively to a specific antigen.

In one embodiment, the sdAbs are from heavy-chain antibodies found in camelids (VHH fragments), or cartilaginous fishes (VNAR fragments), or are obtained by splitting dimeric variable domains into monomers.

Methods for Detection and Diagnosis

The N_SARS-CoV-2 and N_SARS-CoV-1 proteins and the peptides derived from these proteins and antibodies generated against them, can be used for the diagnosis of a SARS-associated coronavirus infection (serological diagnosis; detection of specific antibodies), in particular by an immunoassay, such as an immunoenzymatic method (e.g., ELISA).

The invention encompasses methods comprising identifying a patient infected with a SARS-associated coronavirus infection, providing a serum sample from the patient, contacting the serum with an N_SARS-CoV-2 or N_SARS-CoV-1 protein, and visualizing the antigen-antibody complexes. In a preferred embodiment, the SARS-associated coronavirus infection is identified as SARS-CoV-2. In some embodiments, the patient has been identified as being infected with a SARS-associated coronavirus infection, but lacks detection of the virus by PCR or another nucleic acid amplification technique.

The invention encompasses a composition comprising an N_SARS-CoV-1 protein or the use of an N_SARS-CoV-1 protein for detection and diagnosis of a SARS-CoV-2 coronavirus in a biological sample.

The invention encompasses a composition comprising an N_SARS-CoV-2 protein or the use of an N_SARS-CoV-2 protein for detection and diagnosis of a SARS-CoV-1 coronavirus in a biological sample.

The ability of N_SARS-CoV-2 to bind with high affinity to SARS-CoV-1 allows its use in such methods, particularly for diagnostics of a SARS-CoV-1 infection.

The ability of N_SARS-CoV-1 to bind with high affinity to SARS-CoV-2 allows its use in such methods, particularly for diagnostics of a SARS-CoV-2 infection.

The antibodies and antibody fragments according to the invention, in particular those directed N_SARS-CoV-2 and N_SARS-CoV-1 proteins and the derived peptides, are useful for the direct diagnosis of a SARS-associated coronavirus infection; the detection of the protein(s) of a SARS coronavirus is carried out by an appropriate technique, in particular EIA, ELISA, RIA, immunofluorescence, in a biological sample collected from an individual capable of being infected.

Preferably, the patient has been shown to be infected by SARS-CoV-1 or SARS-CoV-2 by a nucleic acid detection test, such as a PCR or other nucleic acid amplification test.

In one embodiment, the invention comprises a method for the detection of a SARS-associated coronavirus, from a biological sample, which method is characterized in that it comprises bringing a biological sample from a patient infected with a SARS-CoV-1 coronavirus with a N_SARS-CoV-2 protein, and visualizing the antigen-antibody complexes formed. Preferably, the antigen-antibody complexes are visualized by EIA, ELISA, RIA, or by immunofluorescence.

In one embodiment, the invention comprises a method for the detection of a SARS-associated coronavirus, from a biological sample, which method is characterized in that it comprises bringing a biological sample from a patient infected with a SARS-CoV-2 coronavirus with a N_SARS-CoV-1 protein, and visualizing the antigen-antibody complexes formed. Preferably, the antigen-antibody complexes are visualized by EIA, ELISA, RIA, or by immunofluorescence.

In one embodiment, the invention comprises a method for the detection of a SARS-associated coronavirus, from a biological sample, which method is characterized in that it comprises bringing a biological sample from a patient infected with a SARS-CoV-1 or SARS-CoV-2 coronavirus with a N_SARS-CoV-2 and N_SARS-CoV-1 protein, and visualizing the antigen-antibody complexes formed. Preferably, the antigen-antibody complexes are visualized by EIA, ELISA, RIA, or by immunofluorescence using a detection reagent.

In one embodiment, the N_SARS-CoV-2 and N_SARS-CoV-1 protein is attached to an appropriate support, in particular a microplate or a bead.

In one embodiment, the method comprises bringing a biological sample from a subject, preferably a human, infected with a SARS-CoV-1 or SARS-CoV-2 coronavirus into contact with an N_SARS-CoV-2 and/or N_SARS-CoV-1 protein, which is attached to an appropriate support, in particular a microplate or bead, to allow binding to occur; washing the support to remove unbound antibodies; adding a detection reagent that binds to the immunoglobulins bound to N_SARS-CoV-2 and/or N_SARS-CoV-1 protein; and detecting the N_SARS-CoV-2 and/or N_SARS-CoV-1 protein-antibody complexes formed.

In one embodiment, the method for the detection of a SARS-associated coronavirus in a biological sample comprises providing a N_SARS-CoV-2 protein; providing a biological sample from a patient infected with a SARS-CoV-1 coronavirus; contacting said N_SARS-CoV-2 protein with said biological sample; and visualizing the antigen-antibody complexes formed. Preferably, the method comprises an ELISA. Preferably, the N_SARS-CoV-2 protein comprises or consists of the sequence of SEQ ID NO: 1.

In one embodiment, the method for the detection of a SARS-associated coronavirus in a biological sample comprises providing a N_SARS-CoV-1 protein; providing a biological sample from a patient infected with a SARS-CoV-2 coronavirus; contacting said N_SARS-CoV-1 protein with said biological sample; and visualizing the antigen-antibody complexes formed. Preferably, the method comprises an ELISA.

Preferably, the protein-antibody complexes are detected with an antibody or an antibody fragment that binds to human immunoglobulins.

Preferably, the detection reagent comprises a label is selected from a chemiluminescent label, an enzyme label, a fluorescence label, and a radioactive (e.g., iodine) label. Most preferably, the detection reagent is a labeled antibody or antibody fragment that binds to human immunoglobulins.

Preferred labels include a fluorescent label, such as FITC, a chromophore label, an affinity-ligand label, an enzyme label, such as alkaline phosphatase, horseradish peroxidase, or β galactosidase, an enzyme cofactor label, a hapten conjugate label, such as digoxigenin or dinitrophenyl, a Raman signal generating label, a magnetic label, a spin label, an epitope label, such as the FLAG or HA epitope, a luminescent label, a heavy atom label, a nanoparticle label, an electrochemical label, a light scattering label, a spherical shell label, semiconductor nanocrystal label, wherein the label can allow visualization with or without a secondary detection molecule.

Preferred labels include suitable enzymes such as horseradish peroxidase, alkaline phosphatase, beta-galactosidase, or acetylcholinesterase; members of a binding pair that are capable of forming complexes such as streptavidin/biotin, avidin/biotin or an antigen/antibody complex including, for example, rabbit IgG and anti-rabbit IgG; fluorophores such as umbelliferone, fluorescein, fluorescein isothiocyanate, rhodamine, tetramethyl rhodamine, eosin, green fluorescent protein, erythrosin, coumarin, methyl coumarin, pyrene, malachite green, stilbene, lucifer yellow, Cascade Blue, Texas Red, dichlorotriazinylamine fluorescein, dansyl chloride, phycoerythrin, fluorescent lanthanide complexes such as those including Europium and Terbium, cyanine dye family members, such as Cy3 and Cy5, molecular beacons and fluorescent derivatives thereof, as well as others known in the art; a luminescent material such as luminol; light scattering or plasmon resonant materials such as gold or silver particles or quantum dots; or radioactive material include $^{14}C$, $^{123}I$, $^{124}I$, $^{125}I$, $^{32}P$, $^{33}P$, $^{35}S$, or $^{3}H$.

In one embodiment, the antibody or an antibody fragment that binds to human immunoglobulins binds specifically to IgG, IgA, and IgM. In one embodiment, the antibody or an antibody fragment that binds to human immunoglobulins binds specifically to IgG, IgA, or IgM.

The term "antibodies" is meant to include polyclonal antibodies, monoclonal antibodies, fragments thereof, such as F(ab')2 and Fab fragments, single-chain variable fragments (scFvs), single-domain antibody fragments (VHHs or Nanobodies), bivalent antibody fragments (diabodies), as well as any recombinantly and synthetically produced binding partners.

In a preferred embodiment, the antibody is a VHH, preferably an alpaca serum.

In a preferred embodiment, the antibody is a VHH, preferably an alpaca serum.

Preferably, the method comprises comparing the results obtained with a patient serum to positive and negative controls.

Positive controls can include:
Serum from animals (e.g., rabbit, alpaca, etc.) immunized with N_SARS-CoV-2 or N_SARS-CoV-1 protein as described above
N_SARS-CoV-2 or N_SARS-CoV-1 protein as described above.

The method can comprise the use of N_SARS-CoV-2 and N_SARS-CoV-1 proteins to detect novel coronaviruses that do not cross-react with seasonal (non-pathogenic) coronaviruses.

Preferably, the N_SARS-CoV-2 protein comprises the amino acid sequence of the SARS-CoV-2 N protein of NCBI QHO62884.1.

Preferably, the N_SARS-CoV-1 protein comprises the amino acid sequence of the SARS-CoV N protein of NP_828858.

In one embodiment, the N_SARS-CoV-2 protein comprises or consists of the amino acid sequence of SEQ ID NO:1.

In one embodiment, the N_SARS-CoV-1 protein is one of the N proteins described in U.S. Pat. No. 8,343,718, particularly that of SEQ ID NO:37.

In one embodiment, the method comprises an immunocapture method.

In one embodiment, the method comprises attaching a first monoclonal or polyclonal antibody or a fragment thereof, directed against the N_SARS-CoV-2 or N_SARS-CoV-1 protein (capture antibody), incubating the antibody with a biological sample containing a N_SARS-CoV-2 or N_SARS-CoV-1 protein, and detecting the antigen-antibody complexes formed, preferably with a monoclonal antibody (visualizing antibody).

In one embodiment, the biological sample is mixed with the visualizing monoclonal antibody prior to its being brought into contact with the capture antibody. According to one embodiment of said test, the antibody used for the capture of the N_SARS-CoV-2 protein is the monoclonal antibody mAb87, produced by the hybridoma deposited at the CNCM on Dec. 1, 2004 under the number I-3328 or the monoclonal antibody mAb86, produced by the hybridoma deposited at the CNCM on Dec. 1, 2004 under the number I-3329.

In the immunocapture tests according to the invention, it is possible to use, for visualizing the N_SARS-CoV-2 or N_SARS-CoV-1 protein, the monoclonal antibody mAb57, produced by the hybridoma deposited at the CNCM on Dec. 1, 2004 under the number 1-3330, said antibody being conjugated with a visualizing molecule or particle.

In accordance with said immunocapture test, a combination of the antibodies mAb57 and mAb87, conjugated with a visualizing molecule or particle, is used for the visualization of the N_SARS-CoV-2 or N_SARS-CoV-1 protein.

A visualizing molecule may be a radioactive atom, a dye, a fluorescent molecule, a fluorophore, an enzyme; a visualizing particle may be for example: colloidal gold, a magnetic particle or a latex bead.

The subject of the present invention is also a method for the detection of a SARS-associated coronavirus infection, from a biological sample, by indirect IgG ELISA using the N_SARS-CoV-2 or N_SARS-CoV-1 protein, which method is characterized in that the plates are sensitized with an N_SARS-CoV-2 or N_SARS-CoV-1 protein solution at a concentration of between 0.5 and 4 g/ml, preferably to 2 µg/ml, in a 10 mM PBS buffer pH 7.2, phenol red at 0.25 ml/l.

In one embodiment, microtiter are plates were coated by incubation overnight at 4° C. with 5 µg/ml of N proteins. Plates are washed with 0.1% Tween 20 in PBS buffer. Serum or purified Igs are diluted in PBS containing 0.5% gelatin and 0.1% Tween. After 1 h incubation at 37° C., plates are washed again. The bound antibodies are detected by adding a rabbit polyclonal anti-IgGs (obtained by immunizing rabbits with IgGs isolated on protein A and protein G columns) followed by Alkaline Phosphatase labeled goat anti-rabbit immunoglobulins. Enzymatic activity is quantified using pNPP (para-NitroPhenylPhosphate, SigmaAldrich) substrate according to the manufacturer's protocol.

According to one variant of the tests for detecting SARS-associated coronaviruses, these tests combine an ELISA using the N protein, and another ELISA using the S protein.

The subject of the present invention is also an immune complex formed of a polyclonal or monoclonal antibody or antibody fragment as defined above, and of a N_SARS-CoV-2 or N_SARS-CoV-1 protein.

Kits Containing N_SARS-CoV-2 and N_SARS-CoV-1 Proteins

The invention encompasses a SARS-associated coronavirus detection kit, characterized in that it comprises a N_SARS-CoV-2 and N_SARS-CoV-1 protein, as described above, and/or antibodies generated against them.

Preferably, the N_SARS-CoV-2 protein comprises the amino acid sequence of the SARS-CoV-2 N protein of NCBI QHO62884.1.

Preferably, the N_SARS-CoV-1 protein comprises the amino acid sequence of the SARS-CoV N protein of NP 828858.

In one embodiment, the invention comprises a kit for the detection of a SARS-CoV-1 coronavirus, which kit contains a N_SARS-CoV-2 protein and reagents for detection of antigen-antibody complexes.

Preferably, the kit contains a serum of an animal immunized with N_SARS-CoV-2 and/or N_SARS-CoV-1 proteins.

Most preferably, the serum is a rabbit or alpaca serum from an animal immunized with N_SARS-CoV-2 and/or N_SARS-CoV-1 proteins.

In one embodiment, the invention comprises a kit for the detection of a SARS-CoV-2 coronavirus, which kit contains a N_SARS-CoV-1 protein and reagents for detection of antigen-antibody complexes.

Preferably, the kit contains a serum of an animal immunized with N_SARS-CoV-2 and/or N_SARS-CoV-1 proteins.

Most preferably, the serum is a rabbit or alpaca serum from an animal immunized with N_SARS-CoV-2.

Preferably, the kit of the invention comprises an N_SARS-CoV-2 protein comprising the amino acid sequence of the SARS-CoV-2 N protein of NCBI QHO62884.1.

Preferably, the kit of the invention comprises an N_SARS-CoV-1 protein comprising the amino acid sequence of the SARS-CoV N protein of NP 828858.

Preferably, the kit of the invention comprises an N_SARS-CoV-2 protein that comprises or consists of the amino acid sequence of SEQ ID NO:1.

Preferably, the kit of the invention comprises an N_SARS-CoV-1 protein that is one of the N proteins described in U.S. Pat. No. 8,343,718, particularly that of SEQ ID NO: 37.

In one embodiment, the kit comprises both N_SARS-CoV-1 and N_SARS-CoV-2 proteins and an N1 and/or N2 immune serum.

In one embodiment, the kit is a Simple/Rapid test designed for use where a preliminary screening test result is required. The tests can be a test based on agglutination, immuno-dot, immuno-chromatographic and/or immuno-filtration techniques. Preferably, the test is quick and easy to perform, preferably from about 10 minutes to about 2 hours, and requires little or no additional equipment.

Preferably, the kit can be stored at room temperature for extended period of time.

EXAMPLES

Example 1: Production and Purification of SARS-CoV-1 and SARS-CoV-2 Recombinant N Protein SARS-CoV-1 recombinant N protein (N_SARS-CoV-1) was produced using *E. coli* strain BL21 (DE3) pDIA17 transformed with the expression vector pIV2.3N deposited under at the Collection Nationale de Cultures de Microorganismes (CNCM) at the Institut Pasteur, 25, Rue du Docteur Roux, 75724 Paris, FR, on Oct. 23 2003, under the deposit number CNCM I-3117 and purified as previously disclosed in U.S. Pat. No. 8,343,718 (see in particular the protocol disclosed in example 2).

cDNAs encoding the native nucleoprotein antigen (N_SARS-CoV-2) from 2019-nCOV (SARS-CoV-2) was designed base on the Genbank MN908947 sequence publicly available from NBCBI on 20th January 2020. This sequence was then processed to generate an optimized nucleotide sequences for high expression in *E coli*. Optimization process includes codon adaptation, mRNA de novo synthesis and stability, transcription and translation efficiency. Bsa1 and Xho1/EcoR1/Not1 restriction sites were then added at the 5' and 3' ends, respectively, of the nucleotide sequences. The resulting optimised cDNA named "N-Ecoli optimized gene" was synthesized. The Bsa1-Xho1 fragment of the "N-Ecoli optimized gene" has been inserted into Nco1/Xho1-digested pETM-11 vector and the resulting pETM11-Necoli_2019-nCOV (=pETM11/N-nCov *E. coli*) has been used to produce a fusion polypeptide between the SARS-CoV-2 protein and a N-terminally located poly-histidine tag (6 histidine), separated by a TEV cleavage site.

The resulting His6-N_2019-nCOV (N_SARS-CoV-2) polypeptide has the sequence:

(SEQ ID NO: 1)

```
  1  MKHHHHHHPM SDYDIPTTEN LYFQGAMSDN GPQNQRNAPR ITFGGPSDST GSNQNGERSG

61  ARSKQRRPQG LPNNTASWFT ALTQHGKEDL KFPRGQGVPI NTNSSPDDQI GYYRRATRRI

121  RGGDGKMKDL SPRWYFYYLG TGPEAGLPYG ANKDGIIWVA TEGALNTPKD HIGTRNPANN

181  AAIVLQLPQG TTLPKGFYAE GSRGGSQASS RSSSRSRNSS RNSTPGSSRG TSPARMAGNG

241  GDAALALLLL DRLNQLESKM SGKGQQQQGQ TVTKKSAAEA SKKPRQKRTA TKAYNVTQAF

301  GRRGPEQTQG NFGDQELIRQ GTDYKHWPQI AQFAPSASAF FGMSRIGMEV TPSGTWLTYT

361  GAIKLDDKDP NFKDQVILLN KHIDAYKTFP PTEPKKDKKK KADETQALPQ RQKKQQTVTL

421  LPAADLDDFS KQLQQSMSSA DSTQA**
```

Nucleoprotein coding sequences (WT-CoV-2 SARS DNA and E. coli optimized CoV-2 SARS DNA) are cloned into pETM11 vector (EMBL; Dümmler et al (2005), Microb Cell Fact 13; 4:34) or pIVEX2-3 (Roche vector) vectors. The N-recombinant Nucleoprotein of CoV-2-SARS (SARS-CoV-2) is produced in *E. coli* BL21 (DE3) pDIA17 as a fusion protein comprising an N- or C-terminal (His)$_6$ polyhistidine label. Concerning the production of N-recombinant Nucleoprotein with a (His)$_6$ N-terminal label, the following recombinant vectors are used for the transformation of *E. coli* strain BL21 (DE3) pDIA17:

pETM11/N-nCov WT4-(His)$_{6-Nter}$
pETM11/N-nCov WT6-(His)$_{6-Nter}$
pETM11/N-nCov *E. coli* 3-(His)$_{6-Nter}$
pETM11/N-nCov *E. coli* 4-(His)$_{6-Nter}$
pIVEX/nCov WT-(His)$_{6-Nter}$ Clone 1
pIVEX/nCov WT-(His)$_{6-Nter}$ Clone 2

*E. coli* strain BL21 (DE3) pDIA 17 transformed with recombinant plasmid pETM11/N-nCov *E. coli* 3-(His)$_{6-Nter}$ or pETM11/N-nCov *E. coli* 4-(His)$_{6-Nter}$ were deposited at the Collection Nationale de Cultures de Microorganismes (CNCM) at the Institut Pasteur, 25, Rue du Docteur Roux, 75724 Paris, FR, on May 11, 2020, under the deposit numbers CNCM I-5510 and CNCM I-5511, respectively. Cultures in Thomson flasks shaken in LB medium (IPTG induction) and NZytech medium (self-inducible) of *E. coli* BL21 (DE3) pDIA17 strains transformed by the pETM11 vector or by the pIVEX 2.3 vector.

The Thomson flasks are 2.5 L notched flasks allowing cultures of 1 litre of medium to be aerated under good aeration conditions in stirrers.

Production in LB Environment (IPTG Induction)

The 4 strains of *E. coli* BL21 (DE3) pDIA 17 transformed by the pETM11 vector (DMSO no. 1535, 1536, 1537, 1538) are spread on an agar LB Petri dish containing 50 µg/ml kanamycin and 30 µg/ml chloramphenicol. The 2 strains of *E. coli* BL21 (DE3) pDIA17 transformed by the vector pIVEX2.3 (DMSO n° 1539, 1540) are spread on an agar LB Petri dish containing 100 µg/ml ampicillin and 30 µg/ml chloramphenicol. All plates of LB Agar Petri LB are incubated overnight at 37° C. in an oven.

From each of the 6 Petri LB agar plates are inoculated with a platinum handle, 6 pre-cultures of 500 ml of LB medium in 2.5 L Thomson flasks (LB medium plus antibiotics appropriate to each recombinant vector pETM11 and pIVEX2.3). These pre-cultures are shaken at 180 rpm in a Multitron Infors shaker for 15 h at 30° C.

From the 4 LB pre-cultures of BL21 (DE3) pDIA17 strains transformed by the pETM11 vector (DMSO No. 1535, 1536, 1537, 1538) are seeded at an initial cell density equivalent to DOA600=0.2, cultures of 1 L of LB medium containing 50 µg/ml kanamycin and 30 µg/ml chloramphenicol.

From the 2 LB pre-cultures of BL21 (DE3) pDIA17 strains transformed by the pIVEX 2.3 vector (DMSO No. 1539, 1540) are seeded at an initial cell density equivalent to DOA600=0.2, cultures of 1 L of LB medium containing 100 µg/ml ampicillin and 30 µg/ml chloramphenicol.

All these cultures in LB medium are placed under agitation at 180 rpm and 30° C. When the cell density, equivalent to DOA600=0.8 is reached the cultures are induced by addition of 1 mM IPTG and the temperature is maintained at 30° C.

After 2 hours at 30° C. in the presence of the inducer the cultures are stopped. A 10 ml sample of each culture is centrifuged and will be used for analysis on SDS-Page of the total soluble and insoluble protein fractions. The remainder of each culture is centrifuged (15 min at 6000 rpm) and the pellets stored at −80° C.

Production in NZytech Medium (Self-Inducible)

From the 4 LB pre-cultures of BL21 (DE3) pDIA17 strains transformed by the pETM11 vector (DMSO No. 1535, 1536, 1537, 1538) are seeded at an initial cell density equivalent to DOA600=0.2, 1 L cultures in NZytech (self-inducible) medium containing 50 µg/ml kanamycin and 30 µg/ml chloramphenicol.

From the 2 LB pre-cultures of BL21 (DE3) pDIA17 strains transformed by the pIVEX 2.3 vector (DMSO No. 1539, 1540) are seeded at an initial cell density equivalent to DOA600=0.2, 1 L cultures in NZytech (self-inducible) medium containing 100 µg/ml ampicillin and 30 µg/ml chloramphenicol.

Cultures in NZytech medium (self-inducible) are carried out at 37° C. with stirring at 180 rpm.

After 4 hours at 37° C., the cultures are placed at 18° C.

After 15 hours of culture at this temperature of 18° C., the bacterial cultures are stopped. A 10 ml sample of each culture is centrifuged and will be used for analysis on SDS-Page of the total soluble and insoluble protein fractions. The remainder of each culture is centrifuged (15 min at 6000 rpm) and the pellets stored at −80° C.

Cultures in BioPod F200 microfermenters in high cell density HDM medium (IPTG induction) of *E. coli* BL21 (DE3) pDIA17 strains transformed by the pETM11 vector or by the pIVEX 2.3 vector:

The HDM medium is a complex culture medium developed by our Platform specifically designed for the large production of *E. coli* biomass in a bioreactor during batch culture. This buffered medium does not require a regulation of the pH value in culture.

Microfermenters are miniaturized bioreactors allowing to realize 100 ml cultures in high density medium (HDM medium). These micro-fermenters are equipped with mass flow meters and sinter allowing a very efficient micro-bubbling by air progressively enriched with oxygen according to the bacterial growth. These bioreactors are also equipped with Peltier system and PT1000 probe which allow a very reliable regulation of the growth temperature and fast passages from 37° C. to 16° C. during the induction phase. This system of miniaturized bioreactors is a tool for optimizing the culture conditions allowing with a high rate of reliability a scale-up of 100 ml cultures to larger volume reactors (4 L and 16 L in our Platform).

The 2 strains of *E. coli* BL21 (DE3) pDIA 17 transformed by the pETM11 vector (DMSO n° 1535 and 1537) are spread on an agar LB Petri dish containing 50 µg/ml kanamycin and 30 µg/ml chloramphenicol.

The 2 strains of *E. coli* BL21 (DE3) pDIA17 transformed by the vector pIVEX2.3 (DMSO no. 1539, 1540) are spread on an agar LB Petri dish containing 100 µg/ml ampicillin and 30 µg/ml chloramphenicol. All LB agar plates are incubated overnight at 37° C. in an oven.

About 1.5 ml of antibiotic-free LB medium is deposited on each of the agar plates. The bacterial mat of each LB plate is scraped off with a sterile rake. Each bacterial suspension collected is used to inoculate a micro-fermentor containing 100 ml of HDM medium plus antibiotics appropriate for *E. coli* BL21 (DE3) pDIA17 strains transformed by the recombinant pETM11 or pIVEX2.3 vectors. The initial cell density of the bioreactors is equivalent to $A_{600}$=0.8 to 1.

The cultures are grown at a temperature of 37° C., and aeration is set at 0.5 VVM. When the cell density equivalent to DOA600=18 to 20 is reached, the temperature is lowered to 16° C. and IPTG (1 mM) is added to the cultures.

After 15 hours of culture at 16° C. in the presence of the inducer, the bacterial cultures are stopped. A 1 ml sample of each culture is centrifuged and will be used for analysis on SDS-Page of the total soluble and insoluble protein fractions. The remainder of each culture is centrifuged (15 min at 6000 rpm) and the pellets stored at −80° C.

Purification from pETM11/N-nCov E. coli-$(His)_{6-Nter/NZytech}$ Cultures

Data Prot Param:
  MW=48.7 KDa
  pI=9.9
  Ext. coefficient
  Abs 0.1% (=1 g/l): 0.961

Bacterial Pellet Breakage

Take the 9 g pellet with 50 ml buffer A: 50 mM phosphate, 300 mM NaCl, 20 mM imidazole pH8 with 1 Roche EDTA free protease tablet and 5 µl benzonase in the blender/wait incubation at room temperature for approx. 20 min.
  1) Cold breaking with the Cell D 1.3 kbar Cell Disrupter.
  2) Addition of eNASR A (250 µl to 10 mg/ml or 2.5 mg). Incubation at room temperature for about 20 min.
  3) Centrifugation 19000 rpm rotor SS34 1 hour 4° C.
  4) Recovery of the soluble fraction=supernatant for affinity purification on nickel resin.

Treatment of the Soluble Fraction
  1st STEP OF PURIFICATION: AFFINITY IMAC (AKTAPure): 1 column Nickel 5 ml
  1 New 5 ml Protino Ni-NTA column (Macherey Nagel) mounted on AKTA Pure (room temperature)
  Washing of the column in $_{H2O}$: 10 CV
  Column equilibration buffer: Phosphate 50 mM, NaCl 300 mM, imidazole 20 mM pH8: 10 CV
  Loading the 60 ml crude extract onto the 5 ml IMAC column at a rate of 1 ml/min with the AKTA pump
  Flow rate: 1 ml/min
  Washing with Phosphate buffer 50 mM, NaCl 300 mM, imidazole 20 mM, pH8: 10 CV
  Elution:
    Elution Buffer: Phosphate 50 mM, NaCl 300 mM, imidazole 250 mM pH8
    Gradient from 20 to 250 mM imidazole=100% buffer B at 2 ml/min on 10 HP.
    Fractions of 1.5 ml were recovered
    Histogram peak integration for protein quantity estimation Peak of the fractions from A5 to C12, i.e. 48 ml at 3.3 mg/ml. Estimated quantity on unicorn162 mg Fraction analysis at this stage on SDS-Page (FIG. 1A)

| | Well | | | | | | | | |
|---|---|---|---|---|---|---|---|---|---|
| | 1 | 2 | 3 | 4 | 5 | 6 | 7 | 8 | 9 |
| Fraction | PM | EB | FT | LAV | A5 | A6 | A8 | A10 | A12 |
| Qty | | 28 µl | 28 µl | 28 µl | 28 µl | 28 µl | 28 µl | 28 µl | 28 µl |
| | Well | | | | | | | | |
| | 10 | 11 | 12 | 13 | 14 | 15 | 16 | 17 | 18 |
| Fraction | B4 | B6 | B8 | B12 | C3 | C6 | C9 | C12 | D5 |
| Qty | 28 µl | 28 µl | 28 µl | 28 µl | 28 µl | 28 µl | 28 µl | 28 µl | 28 µl |

DO280 nm measurement at 1/10 of the A5 to C9 pool
  DO280=0.364. For 1 g/l, the OD is 0.96 3.64/0.96=3.7 mg/ml. Either for 42 ml: 42 ml×3.7 mg/ml=159 mg total The elution volume will be injected in 8×5 ml on 2 gel filtration columns with 5 ml loops. The columns are installed on the 2 pure AKTAs.

4 runs of gel filtration will be performed per column.

Figure 1B:
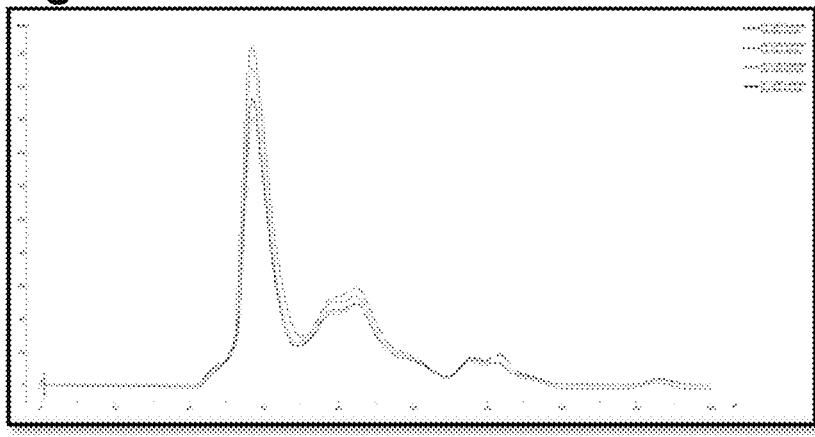
Figure 1C:
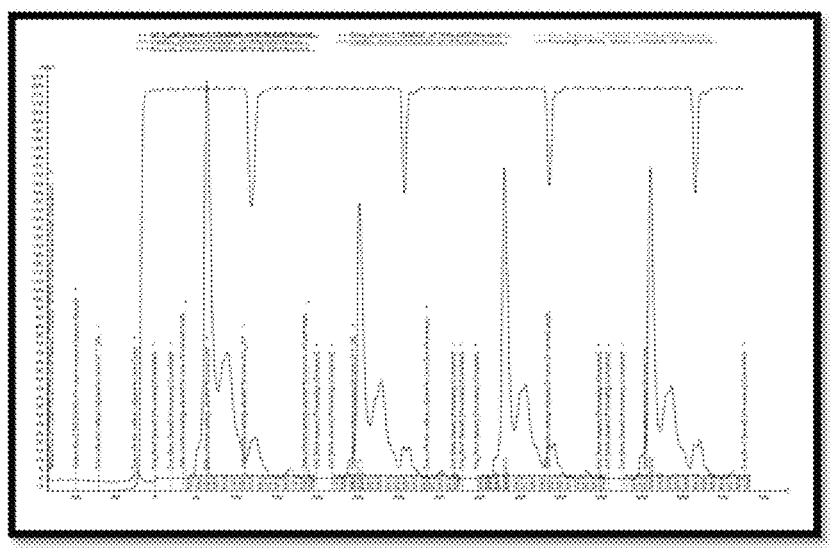

2nd Purification Step: Hiload 16/60 Superdex 200 pg (120 ml) Column Filtration Gel
  Equilibration of the columns with 50 mM Phosphate buffer, 500 mM NaCl pH8
  Flow rate 0.5 ml/min
  Protein injection with 5 ml and 10 ml loops.
  Elution volume for each run 1.4 column volume. Fractions of 1.8 ml.
    Selection of peaks on histograms and integration of peaks for estimation of protein quantity (FIGS. 1B and 1C)

SDS-Page Fraction Removal and Deposition on SDS-Page Gel

Figure 1D:
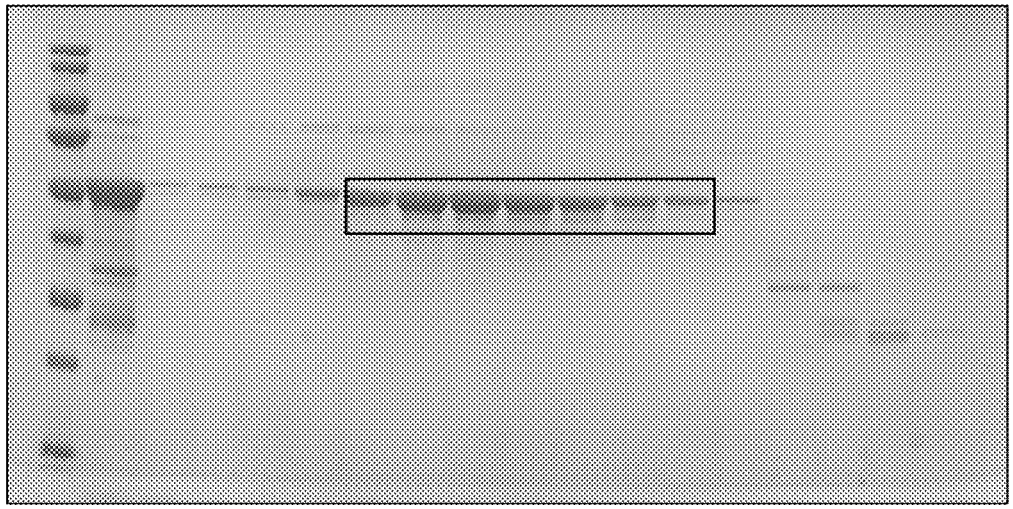

Gel Filtration 3 on Akta 1 (FIG. 1D)

| | Well | | | | | | | | |
|---|---|---|---|---|---|---|---|---|---|
| | 1 | 2 | 3 | 4 | 5 | 6 | 7 | 8 | 9 |
| Fraction | PM | pool | 2H1 | 2H3 | 2H4 | 2H5 | 2H6 | 2H7 | 2H8 |
| Qty | | 28 µl | 28 µl | 28 µl | 28 µl | 28 µl | 28 µl | 28 µl | 28 µl |
| | Well | | | | | | | | |
| | 10 | 11 | 12 | 13 | 14 | 15 | 16 | 17 | 18 |
| Fraction | 2H9 | 2H10 | 2H11 | 2H12 | 3A1 | 3A5 | 3A8 | 3A1 | 3B1 |
| Qty | 28 µl | 28 µl | 28 µl | 28 µl | 28 µl | 28 µl | 28 µl | 28 µl | 28 µl |

Figure 1E:
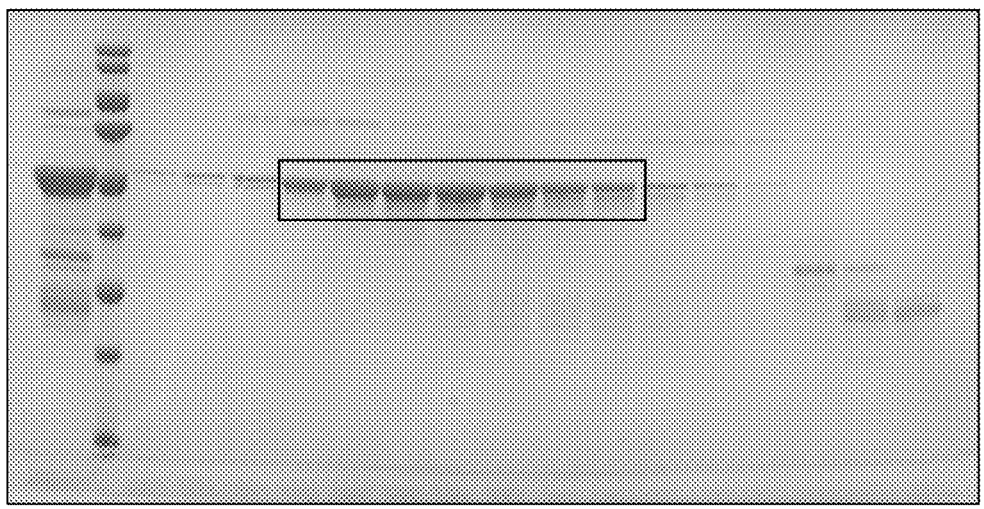
Figure 2A:
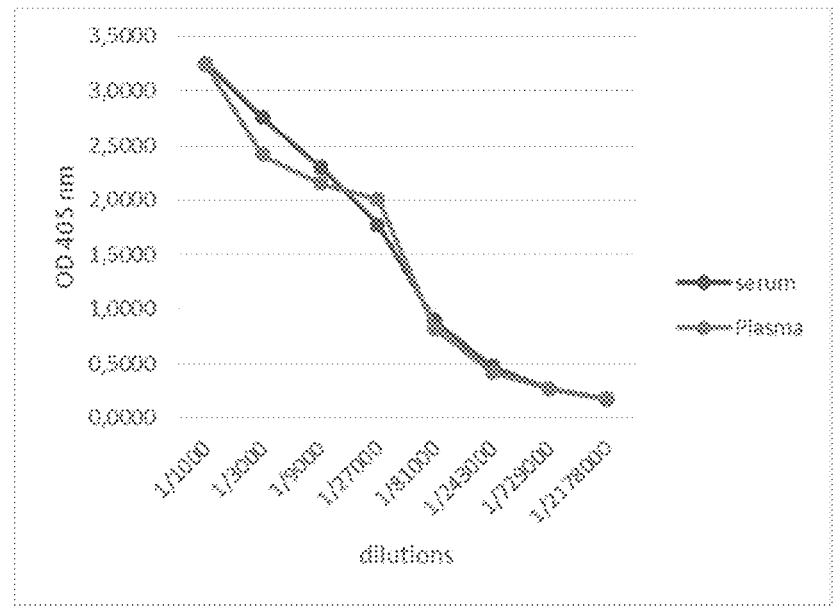
Figure 2B:
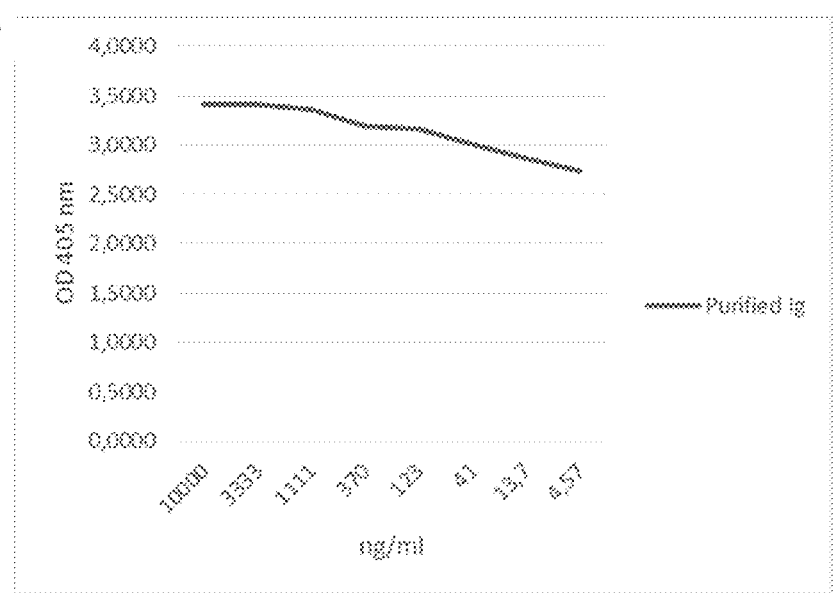
Figure 3A:
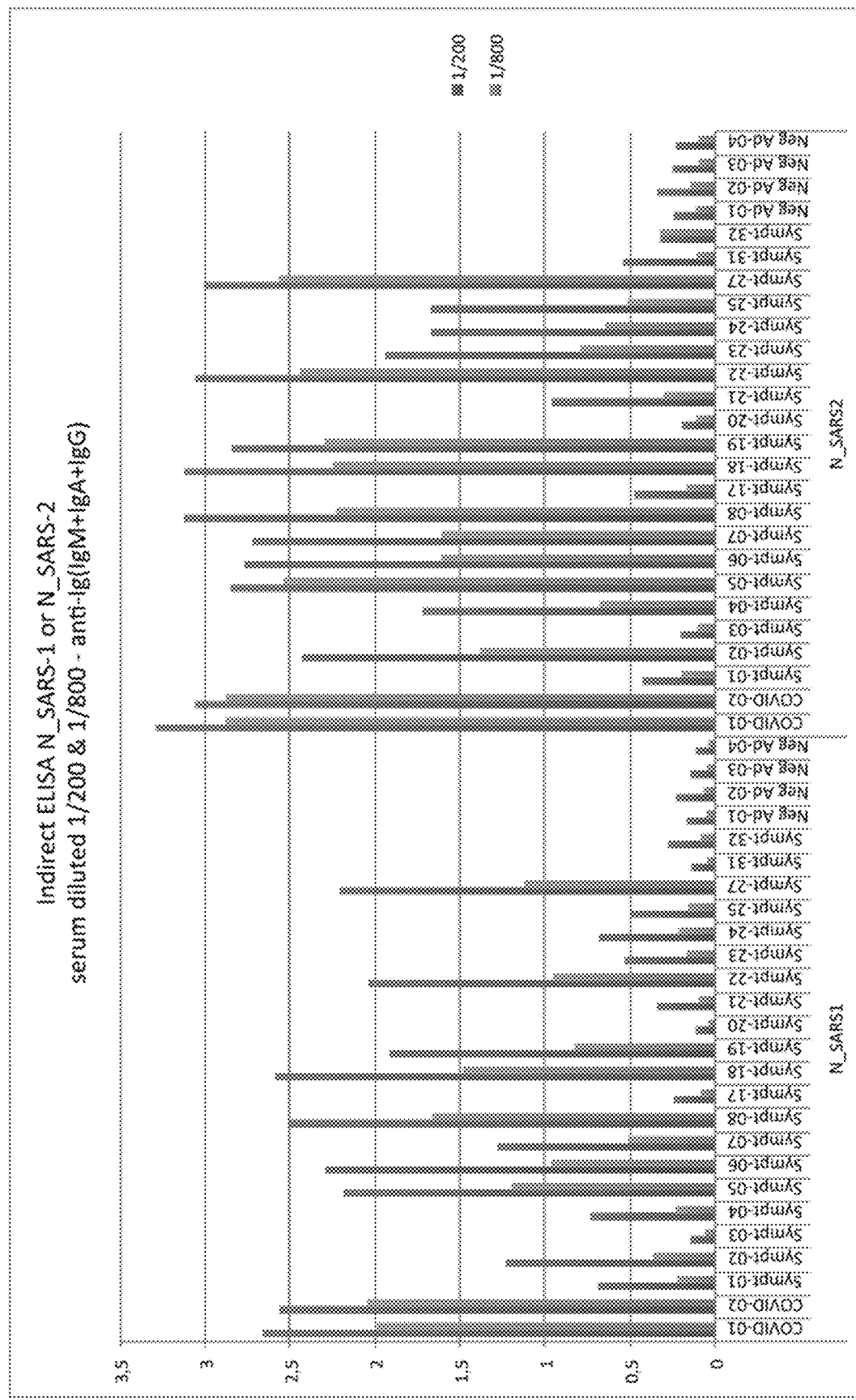
Figure 3B:
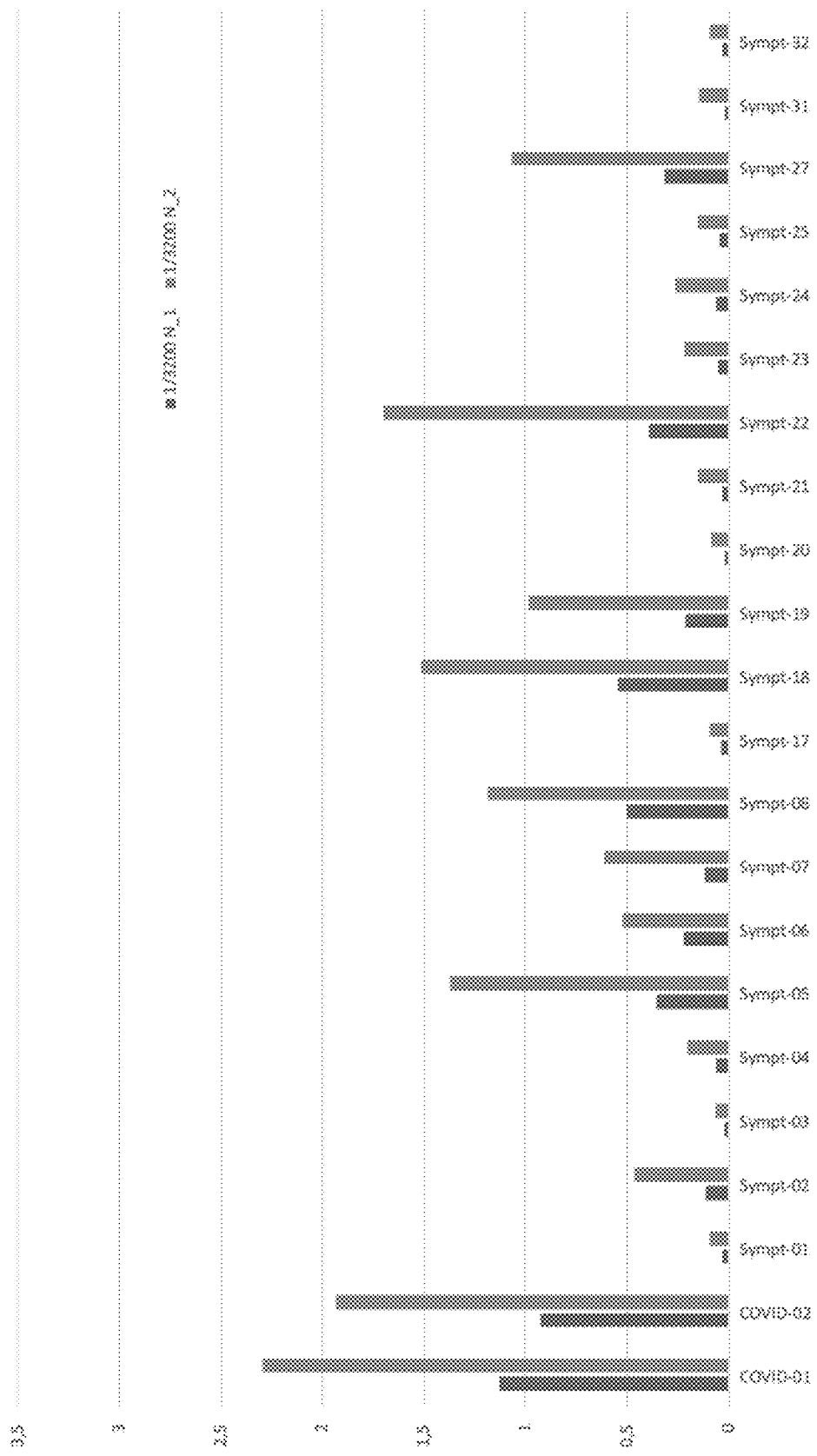
Figure 3C:
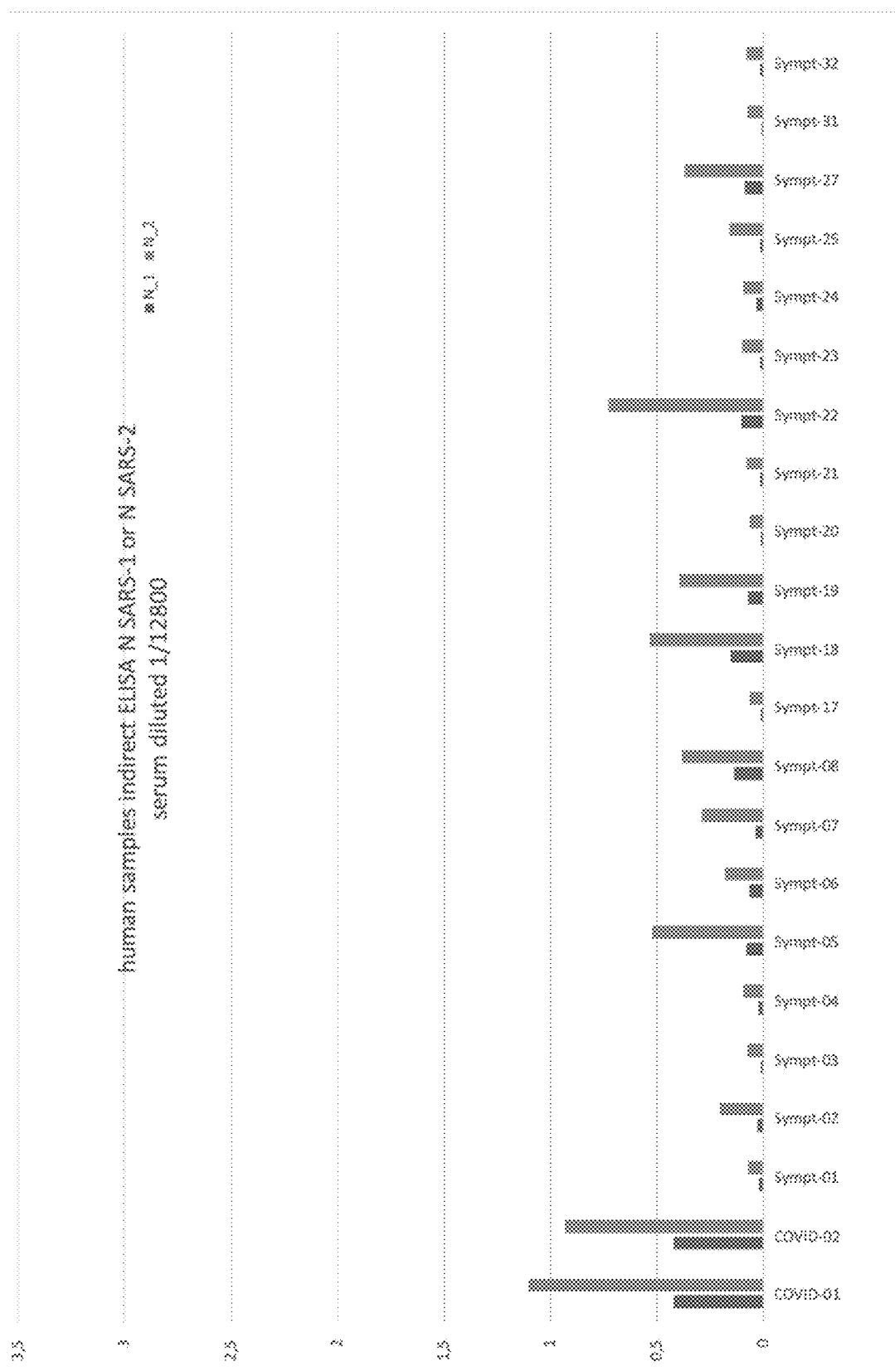

Gel Filtration 6 on Akta 2 (FIG. 1E)

| | Well | | | | | | | | |
|---|---|---|---|---|---|---|---|---|---|
| | 1 | 2 | 3 | 4 | 5 | 6 | 7 | 8 | 9 |
| Fraction | pool | PM | 1H4 | 1H6 | 1H7 | 1H8 | 1H9 | 1H10 | 1H11 |
| Qty | 28 µl | | 28 µl | 28 µl | 28 µl | 28 µl | 28 µl | 28 µl | 28 µl |
| | Well | | | | | | | | |
| | 10 | 11 | 12 | 13 | 14 | 15 | 16 | 17 | 18 |
| Fraction | 1H12 | 2A1 | 2A2 | 2A3 | 2A4 | 2A5 | 2A9 | 2A12 | 2B2 |
| Qty | 28 µl | 28 µl | 28 µl | 28 µl | 28 µl | 28 µl | 28 µl | 28 µl | 28 µl |

Formation of the Gel Fraction Pool Filtration
  GF 1: 1B1 TO 1B8
  GF 2: 2A6 TO 2A12
  GF 3: 2H6 TO 2H12
  GF 4: 3G6 TO 3G12
  GF 5: 1A11 TO1B6
  GF 6: 1H8 TO 2A2
  GF 7: 2G5 TO 2G11
  GF 8: 3F2 TO 3F8.

280 nm OD Measurement of the Pool
  DO280=0.597. For 1 g/l, the OD is 0.96. 0.597/0.96=0.62 mg/ml. Either for 100 ml: 100 ml×0.6 mg/ml=60 mg total Purification and Storage Balance
  N_SARS-CoV-2 purified protein (concentration 0.62 mg/ml in phosphate 50 mM NaCl 500 mM pH8). Pool gel filtration 80 ml split into 4 parts: 20 ml filtered without antiproteases 37 aliquots of 0.5 ml stored at +4° C. (box in cold room; 20 ml filtered with antiproteases 36 aliquots of 0.5 ml stored at +4° C. (box in cold room); 20 ml unfiltered 40 aliquots of 0.5 ml stored at −80° C. (box in freezer room);

20 ml unfiltered+glycerol 50% final 42 aliquots of 1 ml stored at −20° C. (box in freezer room).

E. coli optimized CoV-2 SARS (SARS-CoV-2) DNA cloned into pETM-11 expression vector gave highest protein production yields in *E. coli*. Unexpectedly, the clones pETM11/N-nCov *E. coli* 3-$(His)_{6\text{-}Nter}$ and pETM11/N-nCov *E. coli* 4-$(His)_{6\text{-}Nter}$ were able to achieve high level production without protein aggregation.

Example 2: Preparation of Monospecific Polyclonal Antibodies Directed Against SARS-CoV-1 and SARS-CoV-2 Recombinant N Proteins The preparation of monospecific polyclonal antibodies directed against SARS-CoV-1 recombinant N protein (N1 protein) has been disclosed previously in U.S. Pat. No. 8,343,718 (see in particular the rabbit immunization protocol disclosed in example 4). Monospecific polyclonal antibodies directed against SARS-CoV-2 recombinant N protein (N2 protein) were prepared in alpaca (*Lama pacos*) according to the following protocol. Monospecific polyclonal antibodies directed against SARS-CoV-1 and SARS-CoV-2 recombinant N proteins are useful as positive controls in SARS-CoV-1 immunodiagnostic assays.

1. Material and Methods 1.1 Immunization

125 μg of SARS-CoV-2 recombinant Nucleoprotein (N) prepared according to example 1, in a total volume of 250 μl was mixed with 250 μl of Freund complete adjuvant for the first immunization, and with 250 μl of Freund incomplete adjuvant for the following immunizations. One young adult alpaca (*Lama* pacos) named ANU was immunized at days 1, 19 and 26 with the immunogen. The alpaca was bled at day 33. The immune response was monitored by titration of serum and plasma samples by ELISA on coated Nucleoprotein as disclosed below.

1.2 Purification of Anti-N Alpaca Polyclonal Antibodies

Five mgs of SARS-CoV-2 recombinant N protein were bound on Cyanogen Bromide-activated sepharose 4B (GE Healthcare Life science) according to the manufacturer's instructions. Twenty ml of plasma were incubated with the beads for 2 hours, the beads were washed extensively with PBS until the OD280=0. Then Glycine/HCl 0.1M pH 2.8 was added and the OD280 was monitored. Each fractions of 1 ml were neutralized with 100 μl of Tris 2M. The positive fractions were pooled and dialysed against PBS. An ELISA was performed by coating the Nucleoprotein as disclosed below.

1.3 ELISA

Microtiter plates were coated by incubation overnight at 4° C. with 5 μg/ml of SARS-CoV-2 recombinant N protein. Plates were washed with 0.1% Tween 20 in PBS buffer. Serum or purified Igs were diluted in PBS containing 0.5% gelatin and 0.1% Tween. After 1 h incubation at 37° C., plates were washed again. The bound alpaca antibodies were detected by adding a rabbit polyclonal anti-alpaca IgGs (obtained by immunizing rabbits with alpaca IgGs isolated on protein A and protein G columns) followed by Alkaline Phosphatase labeled goat anti-rabbit immunoglobulins. Enzymatic activity was quantified using pNPP (para-NitroPhenylPhosphate, SigmaAldrich) substrate according to the manufacturer's protocol.

2. Results

FIG. 2A shows the binding of serum and plasma of alpaca ANU and FIG. 2B the binding of purified anti-N2 polyclonal antibodies on SARS-CoV-2 nucleoprotein (N2 protein). The titer of the serum is very high (about 1/243000) and as low as 4 μg of polyclonal Ig can detect the bound SARS-CoV-2 nucleoprotein. The lecture was performed after 15 min.

Example 3: Comparison of SARS-CoV-2 N and SARS-CoV-1 N Indirect ELISA for Detection of SARS-CoV-2 Infection in Patients Sera

1. Material and Methods

Plates are coated with 50 μl of SARS-CoV-2 N protein at 1 μg/ml or SARS-CoV-1 N protein at 1 μg/ml on PBS1× over-night at 4° C. Plates are washed 4 times with 300 μl PBSTween 0.1% (PBST), blocked with 50 μl PBST 3% fat-free milk (PBSTL) for 1 h at 37° C. and blocking solution is removed. 50 μl of patient test serum diluted in PBSTL, at varying dilutions (1/200 generally) is then added and incubated for 1 hr at 37° C. Plates are washed 3 times with 300 μl PBST. 50 μl peroxidase-conjugated anti-human Ig (Ig total, IgG specific, IgM specific or IgA specific) diluted according to manufacturer's instructions in PBSTL is then added and incubated for 1 h at 37° C. Plates are washed 3 times with 300 μl PBST. 50 μl TMB substrate prepared according to manufacturer's instructions is then added and incubated for 10 minutes RT in the dark. 50 μl H3PO4 are then added on the plate are read at 450 nm and 620 nm.

2. Results

Human serum samples were tested in indirect ELISA using SARS-CoV-2 N protein compared to SARS-CoV-1 N protein.

Tested samples were from the following groups:

- 2 CoVID patients (CoVID-01 and CoVID-02): hospitalized patients with confirmed SARS-CoV-1 2 infection (severe cases)
- 20 symptomatic (Sympt-01 to Sympt-20): patients with mild CoVID-like symptoms, sampled during symptoms or after symptoms disappearance (NOT tested for viral RNA)
- 2 prepandemic adults (Neg Ad-01 and Neg Ad-02).

Various serum dilutions were tested (1/200; 1/800; 1/3200; 1/12800).

The results presented in FIG. 3A to 3C show that both SARS-CoV-2 N and SARS-CoV-1 N can detect SARS-CoV-2 infection with good sensitivity and specificity in patients with mild or severe CoVID infection. SARS-CoV-1 N which has already been confirmed to have no cross reactivity with other seasonal coronaviruses is unexpectedly able to cross react with serum of patients with mild or severe SARS-CoV-2 (COVID) infection.

The robustness of the indirect ELISA assay was confirmed using SARS-CoV-2 N protein on cohorts of 180 CoVID patients and 200 negative individuals (Table 1).

TABLE 1

Indirect ELISA assay using SARS-COV-2 N on CoVID patients cohort

| Positivity threshold (OD) | Percentile negative cohort | Negative > threshold | Patients > threshold |
|---|---|---|---|
| 1.788 | 99% | 2 (1%) | 139 (76%) |
| 0.97 | 95%-96% | 9 (4%) | 147 (80%) |

TABLE 1-continued Indirect ELISA assay using
SARS-COV-2 N on CoVID patients cohort

|  | Positivity threshold (OD) | Percentile negative cohort | Negative > threshold | Patients > threshold |
|---|---|---|---|---|
| Number of tested sera |  |  | 203 | 183 |

The indirect ELISA assays allows the detection of 80% of the CoVID patients with a good specificity.

Figure 4B:
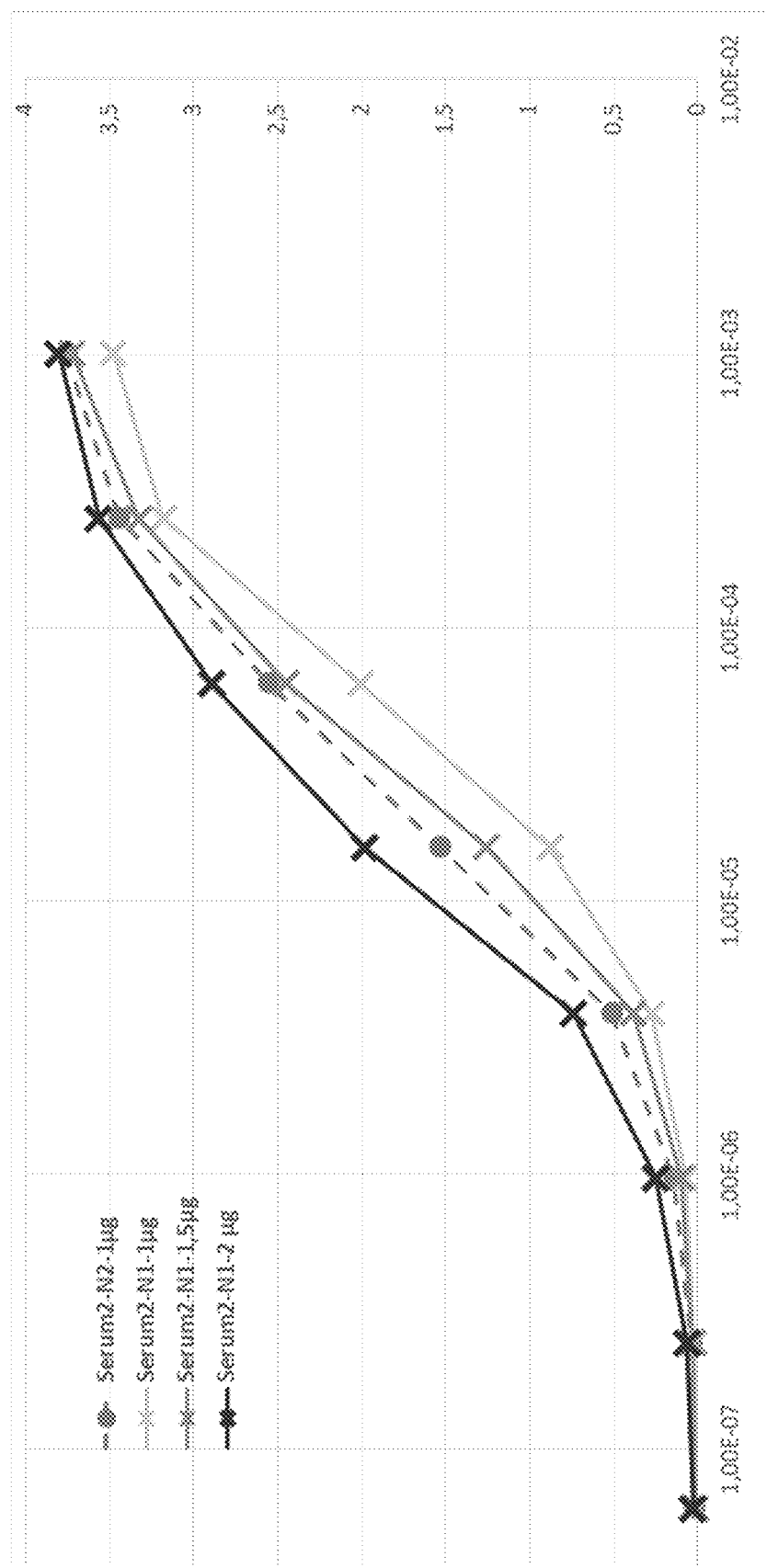
Figure 4C:
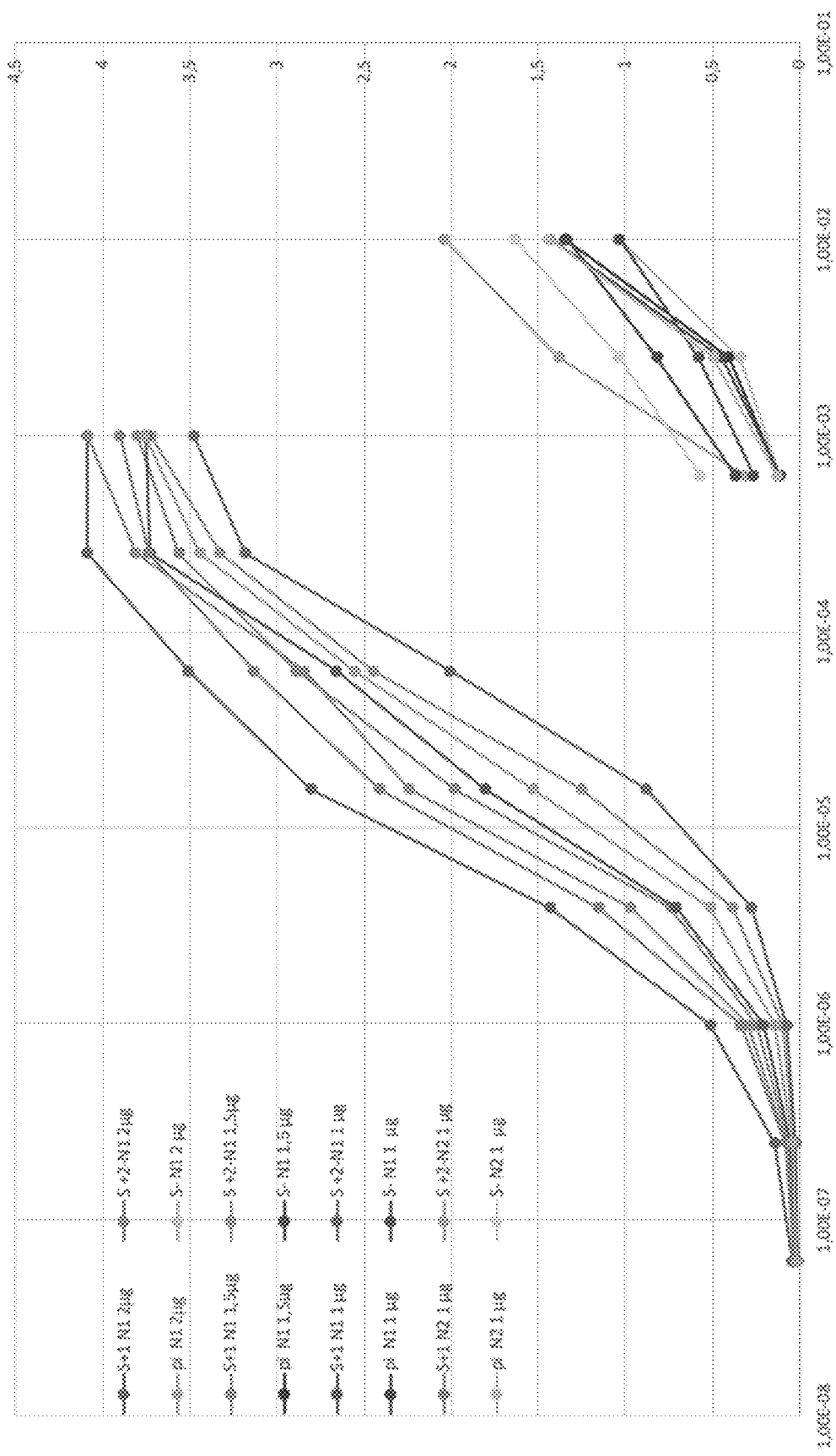
Figure 5:
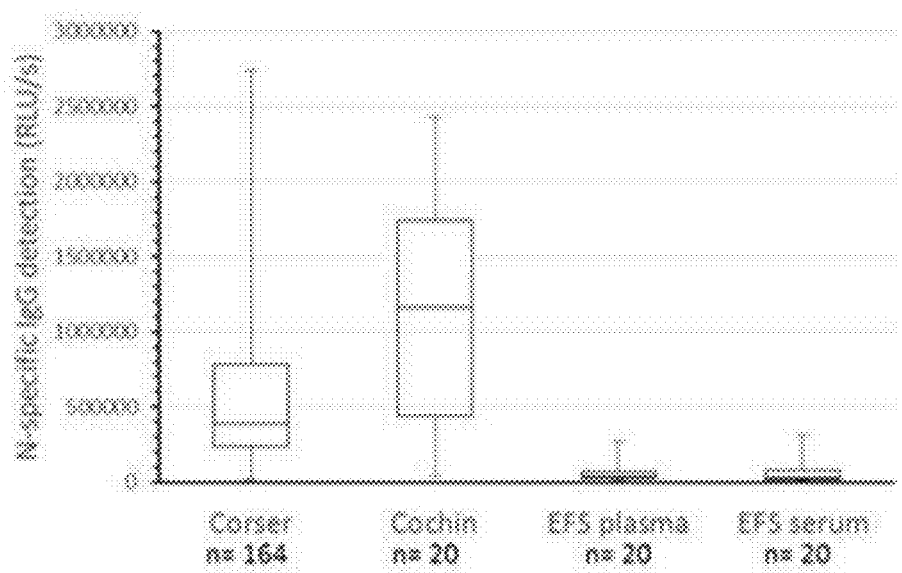
Figure 6:
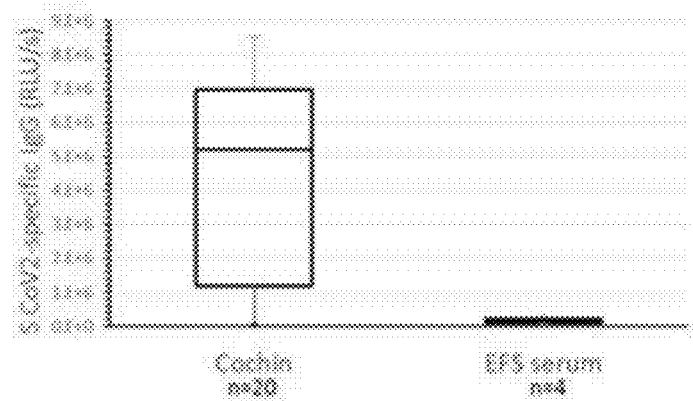
Figure 7:
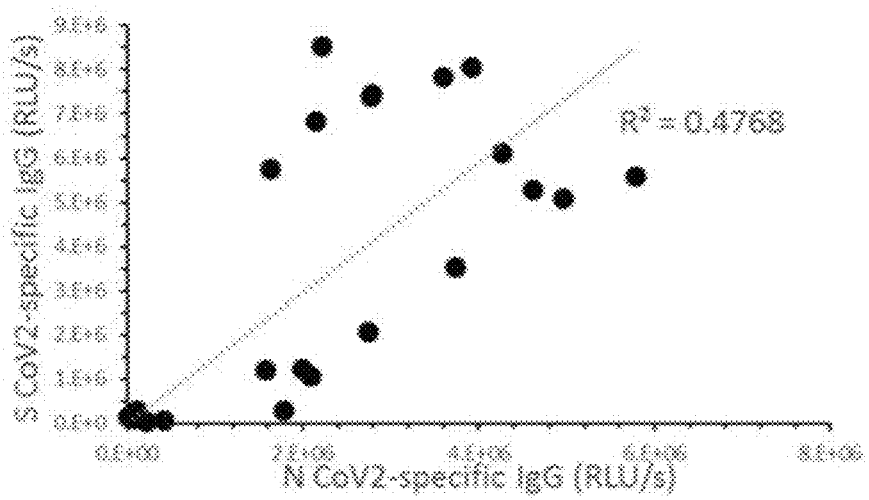
Figure 8:
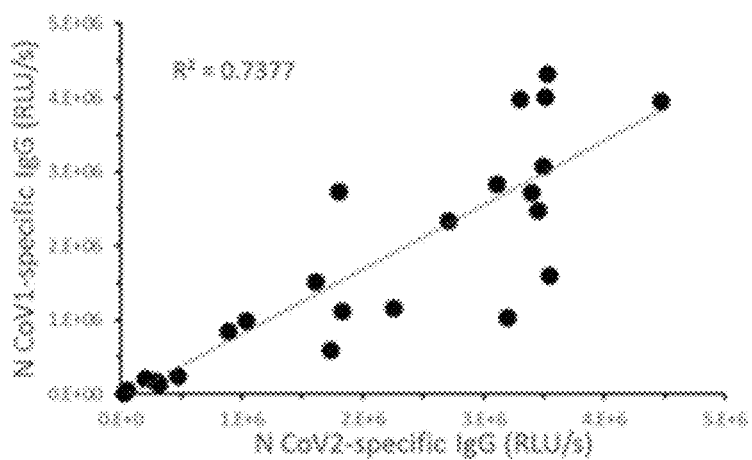
Figure 9:
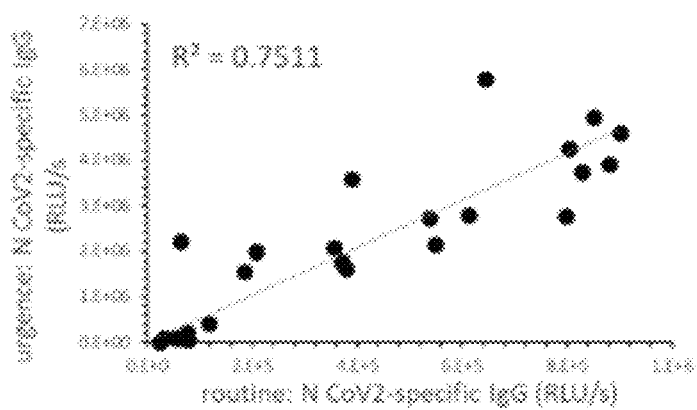

Example 4: Comparison of SARS-CoV-2 N and SARS-CoV-1 N Indirect ELISA for Detection of Anti SARS-CoV-1 Antibodies Rabbit hyperimmune monospecific polyclonal antibodies directed against SARS-CoV-1 virions were tested in the indirect ELISA assay disclosed in example 3 using 1 µg/ml, 1.5 µg/ml or 2 µg/ml of SARS-CoV-1 or 1 µg/ml of SARS-CoV-2 recombinant N protein. The results presented in FIG. 4A to 4C shows that SARS-CoV-2 N is unexpectedly able to cross react with anti SARS-CoV-1 antibodies and can detect anti SARS-CoV-1 antibodies with a good sensitivity and a good specificity.

We claim:

1. A kit for detection of a severe acute respiratory syndrome (SARS)-associated coronavirus infection in a biological sample comprising:
   a severe acute respiratory syndrome-associated coronavirus 2 nucleocapsid protein (SARS-CoV-2 N protein) fused to a N-terminally located poly-histidine tag containing 6 histidines, made by a process comprising expressing and purifying said SARS-CoV-2 N protein fused to a N-terminally located poly-histidine tag containing 6 histidines from *Escherichia coli* (*E. coli*) strain BL21 (DE3) pDIA17 transformed with recombinant plasmid pETM11/N-nCov *E. coli* 3-(His)$_{6-Nter}$ or pETM11/N-nCov *E. coli* 4-(His)$_{6-Nter}$ deposited at the Collection Nationale de Cultures de Microorganismes (CNCM) at the Institut Pasteur, 25, Rue du Docteur Roux, 75724 Paris, France, on May 11, 2020, under the deposit numbers CNCM 1-5510 and CNCM 1-5511, respectively; and
   a severe acute respiratory syndrome-associated coronavirus 2 spike protein (SARS-CoV-2 S protein).

2. A method for detection of a severe acute respiratory syndrome (SARS)-associated coronavirus infection in a biological sample comprising:
   providing a biological sample;
   contacting the biological sample with the SARS-CoV-2 N and SARS-CoV-2 S proteins of the kit of claim 1; and
   detecting antigen-antibody complexes formed between antibodies in the biological sample and the SARS-CoV-2 N and SARS-CoV-2 S proteins.

3. The method of claim 2, wherein the antibodies in the biological sample are immunoglobulin G (IgG).

4. The method of claim 2, wherein the antibodies in the biological sample are immunoglobulin M (IgM).

5. The method of claim 2, wherein the antibodies in the biological sample are immunoglobulin A (IgA).

6. The method of claim 2, wherein the antibodies in the biological sample are IgG, IgM and IgA.

7. The method of claim 2, wherein detecting antigen-antibody complexes comprises an enzyme-linked immunoassay.

8. The method of claim 2, wherein detecting antigen-antibody complexes comprises a lateral flow immunoassay.

9. The method of claim 2, wherein detecting antigen-antibody complexes comprises a bead-based immunoassay.

10. The method of claim 2, wherein detecting antigen-antibody complexes comprises a multiplex bead-based immunoassay.

11. The method of claim 2, wherein the SARS-CoV-2 N protein comprises SEQ ID NO:1.

12. The method of claim 2, wherein the SARS-CoV-2 N protein consists of SEQ ID NO: 1.

13. The method of claim 2, wherein the biological sample is obtained from an individual suspected to be infected with a SARS-associated coronavirus.

14. The method of claim 2, wherein the biological sample is obtained from an individual infected with a SARS-associated coronavirus.

15. The method of claim 2, wherein the biological sample is obtained from an individual infected with a SARS-CoV-2.

16. The method of claim 2, wherein the biological sample is mixed with a visualizing monoclonal antibody prior to its being brought into contact with a capture antibody.

17. The method of claim 2, wherein the antigen-antibody complexes are detected with an antibody or an antibody fragment that binds to human immunoglobulins.

18. The method of claim 17, wherein the antibody or an antibody fragment that binds to human immunoglobulins is enzymatically labeled.

* * * * *